United States Patent
Imaizumi et al.

(10) Patent No.: US 9,133,496 B2
(45) Date of Patent: Sep. 15, 2015

(54) MATERIAL FOR SCREENING FOR COMPOUND ACTING ON ION CHANNEL AND USE THEREOF

(75) Inventors: Yuji Imaizumi, Nagoya (JP); Masato Fujii, Nagoya (JP); Susumu Ohya, Nagoya (JP); Hisao Yamamura, Nagoya (JP)

(73) Assignees: PUBLIC UNIVERSITY CORPORATION NAGOYA CITY UNIVERSITY, Aichi (JP); CHANNELOSEARCH TECHNOLOGY, Aichi (JP)

( * ) Notice: Subject to any disclaimer, the term of this patent is extended or adjusted under 35 U.S.C. 154(b) by 0 days.

(21) Appl. No.: 13/807,464

(22) PCT Filed: Jun. 29, 2011

(86) PCT No.: PCT/JP2011/064967
§ 371 (c)(1),
(2), (4) Date: Mar. 18, 2013

(87) PCT Pub. No.: WO2012/002460
PCT Pub. Date: Jan. 5, 2012

(65) Prior Publication Data
US 2013/0183709 A1   Jul. 18, 2013

(30) Foreign Application Priority Data
Jun. 29, 2010 (JP) .................................. 2010-147255

(51) Int. Cl.
| C12Q 1/68 | (2006.01) |
| C12Q 1/02 | (2006.01) |
| C07K 14/705 | (2006.01) |
| G01N 33/68 | (2006.01) |
| C12N 5/00 | (2006.01) |
| C12N 5/02 | (2006.01) |
| C12N 5/071 | (2010.01) |
| C12N 5/10 | (2006.01) |
| C12N 5/16 | (2006.01) |
| G01N 33/48 | (2006.01) |

(52) U.S. Cl.
CPC .............. *C12Q 1/025* (2013.01); *C07K 14/705* (2013.01); *G01N 33/6872* (2013.01); *G01N 2500/10* (2013.01); *G01N 2510/00* (2013.01)

(58) Field of Classification Search
None
See application file for complete search history.

(56) References Cited

U.S. PATENT DOCUMENTS

| 6,686,193 B2* | 2/2004 | Maher et al. ............... 435/285.2 |
| 6,828,101 B2* | 12/2004 | Miyake et al. ............... 435/6.17 |
| 7,611,850 B2* | 11/2009 | Maher et al. ................. 435/7.2 |
| 2008/0182288 A1 | 7/2008 | Adorante et al. |

FOREIGN PATENT DOCUMENTS

| JP | A-2006-126073 | 5/2006 | |
| JP | A-2009-131247 | 6/2009 | |
| WO | WO 03/006103 A2 | 1/2003 | |
| WO | WO 2005/069008 A1 | 7/2005 | |
| WO | WO 2005/108598 A1 | 11/2005 | |
| WO | 2010/071983 A1 * | 7/2010 | ........... C07K 14/705 |

OTHER PUBLICATIONS

González et al., "Cell-based assays and instrumentation for screening ion-channel targets" 4(9) Drug Discovery Today 431-439 (1999).*
Farre et al., "Ion channel screening—automated patch clamp on the rise" 5(1) Drug Discovery Today: Technologies e23-e28 (2008).*
Jongsma et al., "Channelopathies: Kir2.1 mutations jeopardize many cell functions" 11 Current Biology R747-R750 (2001).*
Sanguinetti et al., "hERG potasium channels and cardiac arrythmia" 440 Nature 463-469 (2006).*
Terstappen, "Ion channel screening technologies today" 2(2) Drug Discovery Today: Technologies 133-140 (2005).*
Dale et al., "Population patch clamp electrophysiology: a breakthrough technology for ion channel screening," *Molecular BioSystems*, 2007, vol. 3, pp. 714-722.
Saito et al., "ES cells for Drug Discovery," *Gekkan Medical Science Digest*, 12 Gatsu Special Extra Issue, Dec. 25, 2007, vol. 33, No. 14, whole No. 433, pp. 33(1272)-36(1275).
Mohan et al., "Toxin detection based on action potential shape analysis using a realistic mathematical model of differentiated NG108-15 cells," *Biosensors and Bioelectronics*, 2006, vol. 21, Issue 9, pp. 1804-1811.
Wallis, "Non Clinical Pharmacology—To Cover Testing Paradigms and Latest ICH Thinking (ICH S7B)," QT Symposium: Non Clinical Pharmacology and Clinical Assessment of QT Prolongation, Jun. 25, 2004, vol. 31, Suppl 20, pp. 279-295.
Fujii et al., "Kaihen Idenshi Hatsugen Saibo o Mochiita Saiboshi Sokutei ni yoru Shinki Ion Channel Hyoteki Soyaku Screening-kei no Kaihatsu," Dai 118 Kai The Japanese Pharmacological Society Kinki Bukai Program Yoshishu, Nov. 19, 2010, p. 60, C-15.
Fujii et al., "Kaihen Idenshi Hatsugen Saibo o Mochiita Saiboshi Sokutei ni yoru Shinki Ion Channel Hyoteki Soyaku Screening-kei no Kaihatsu," The Pharmaceutical Society of Japan Dai 131 Nenkai Yoshishu 3, Mar. 5, 2011, p. 81, 30X-pm11.
International Search Report issued in International Application No. PCT/JP2011/064967 dated Aug. 9, 2011. (with translation).
Written Opinion issued in International Application No. PCT/JP2011/064967 dated Aug. 9, 2011. (with translation).
Feb. 3, 2014 European Search Report issued in Application No. 11800922.4.

(Continued)

Primary Examiner — Celine Qian
Assistant Examiner — Nancy J Leith
(74) Attorney, Agent, or Firm — Oliff PLC

(57) ABSTRACT

An object of the present invention is to provide a screening system that targets ion channels and has superior efficiency. The present invention provides a material for screening for compounds that act on a target ion channel, comprising cells which retain at least one first DNA encoding a voltage-dependent Na ion channel that has been inhibited from being inactivated, and in which a K ion channel has been activated so that a resting membrane potential becomes deeper in a negative direction.

6 Claims, 17 Drawing Sheets

(56) References Cited

OTHER PUBLICATIONS

Feb. 28, 2014 Office Action issued in Chinese Application No. 201180041709.0 (with English Translation).
Hartmann et al., "Effects of III-IV linker mutations on human heart Na+ channel inactivation gating," Circulation Research 75: 114-122 (1994).
De Boer et al., "Inhibition of cardiomyocyte automaticity by electrotonic application of inward rectifier current from Kir2.1 expressing cells," Med Biol Eng Comput 44: 537-542 (2006).
Dec. 11, 2014 Office Action issued in European Application No. 11 800 922.4.
Takahashi et al., "Role of Sodium Ion Influx in Depolarization-Induced Neuronal Cell Death by High KCl or Veratridine," European Journal of Pharmacology, vol. 372, pp. 297-304, 1999.

* cited by examiner (a)

(b)

Inhibition of High K⁺ Stimulation Induced by
Lidocaine in hERG-HEK-Kir-mutated Nav Cells

MATERIAL FOR SCREENING FOR COMPOUND ACTING ON ION CHANNEL AND USE THEREOF

CROSS-REFERENCE TO RELATED APPLICATION(S)

This application claims priority on Japanese Patent Application No. 2010-147255 filed on Jun. 29, 2010, the contents of which are incorporated herein by reference.

TECHNICAL FIELD

The present invention relates to a material for screening for compounds acting on ion channels and to the use thereof, and more particularly, relates to a material containing cells that can be used to screen for compounds acting on ion channels (including membrane transport proteins) and a screening method using that material.

DESCRIPTION OF RELATED ED ART

Ion channels have physiologically important functions. The discovery of agonists and inhibitors that act on ion channels by targeting these ion channels is expected to provide useful drugs. A known example of a method for evaluating screening systems for drugs targeting such ion channels, for example, voltage-dependent ion channels is a fluorescent membrane potential measurement method that detects changes in membrane potential in cells with a voltage-dependent fluorescent dye (Japanese Patent Application Laid-open No. 2006-126073). In addition, a patch clamp method for electrically detecting membrane potential by adhering (sealing) a glass electrode to a cell membrane is also known. Moreover, an automated patch clamp method has recently been developed which uses a multi-well patch plate having an opening corresponding to the end of a glass electrode in each well, to detect membrane potential by automatically sealing a cell membrane and patch electrode in each well (Tim J. Dale et al., Mol. Biosyst. 2007, 3, 714-722).

There were cases in which, although conventional fluorescent membrane potential measurement methods were suitable for evaluation of large numbers of specimens, there were limitations on their measurement accuracy and the range of applicable ion channels. In addition, although the patch clamp method has high measurement accuracy and allows a large amount of information to be obtained from measurements, it had poor efficiency due to the small number of specimens able to be measured at one time. Moreover, although the automated patch clamp method employs a structure that allows a large number of specimens to be evaluated simultaneously, the efficiency of the patch is low, thereby making this method unsuitable for high-throughput screening. In addition, the automated patch clamp method also has the problems of high equipment and running costs.

In the case of screening targeted at ion channels, since endogenous ligands are ions, it is difficult to predict a structure capable of binding to a target. Consequently, when constructing a screening system that targets ion channels, high-throughput that allows application of a large number of test compounds is even more important in comparison with the case of targeting receptors and other proteins. In addition, in the case of screening that targets ion channels, ligand optimization is frequently difficult, thereby resulting in the need for measurement accuracy simultaneous to high throughput.

However, as has been previously described, conventional fluorescent membrane potential measurement methods for measuring minute changes in membrane potential in cells had problems with accuracy and applicable range, while the automated patch clamp method had problems with efficiency and costs. Thus, a screening system that targets ion channels has yet to be constructed that demonstrates favorable accuracy and superior efficiency.

BRIEF SUMMARY OF INVENTION

An object of the disclosure of the present description is to construct a screening system that targets ion channels and has superior efficiency.

The inventors of the present invention noticed that screening systems targeting ion channels are forced to use evaluation techniques based on the detection of the membrane potential of living cells, and that problems with these evaluation techniques make it difficult to construct a screening system. Various studies were therefore conducted with the aim of constructing a screening system capable of applying a simpler evaluation technique instead of these conventional evaluation techniques. As a result, the inventors of the present invention found that, once depolarization is induced with a stimulus from outside cells, the cells which undergo cell death due to an ion concentration change in the cells, and typically due to an increase in intracellular sodium (Na) ion concentration, as a medium (screening material) for detecting the action of a test compound on an ion channel, makes it possible to detect activation or inhibition by the test compound on the ion channel by using cell death or a sustained action potential that leads to cell death or is equivalent to cell death as an indicator. The following aspects are provided according to the disclosure of the present description.

According to the disclosure of the present description, a material for screening for compounds is provided that comprises cells which act on a target ion channel, which retain at least one first DNA encoding a voltage-dependent Na ion channel that has been inhibited from being inactivated, and in which a K channel has been activated so that a resting membrane potential becomes deeper in a negative direction.

In addition, according to the disclosure of the present description, a screening method is provided that comprises a step of using the above-mentioned cells of the above-mentioned screening material to detect an action of a test compound on the above-mentioned target ion channel by using viability or death of the above-mentioned cells, as an indicator.

Moreover, according to the disclosure of the present description, a device for screening for compounds that act on ion channels is provided that comprises a cell housing unit provided with one or more regions that house cells, and a measurement unit that measures death of the above-mentioned cells in the one or more regions.

BRIEF DESCRIPTION OF DRAWINGS

FIG. 2A showing the current-voltage relationship before and after administering a specific blocker of the Kir 2.1 channel in the form of 100 μM Ba ions, while FIG. 2B showing changes in membrane potential before and after administration of 100 μM Ba ions.

FIG. 3A showing the results for the wild type, while FIG. 3B showing the results for the mutant type.

FIG. 4A showing the results for the wild type, while FIG. 4B showing the results for the mutant type.

DETAILED DESCRIPTION OF INVENTION

The disclosure of the present description relates to a screening system targeted at ion channels, and more specifically, relates to a material for screening comprising cells able to be used for screening for compounds that act on ion channels (membrane transport proteins), a screening method that uses that material, and a screening device. According to the disclosure of the present description, action on a target ion channel during screening can be detected by the cell death of cells constructed for screening. Namely, a mechanism for controlling cell death is imparted in which cell death occurs due to prolongation of action potential occurring due to transient induction of depolarization. Namely, the disclosure of the present description uses this mechanism for controlling cell death as means for detecting action of a test compound on a target ion channel.

Figure 1:
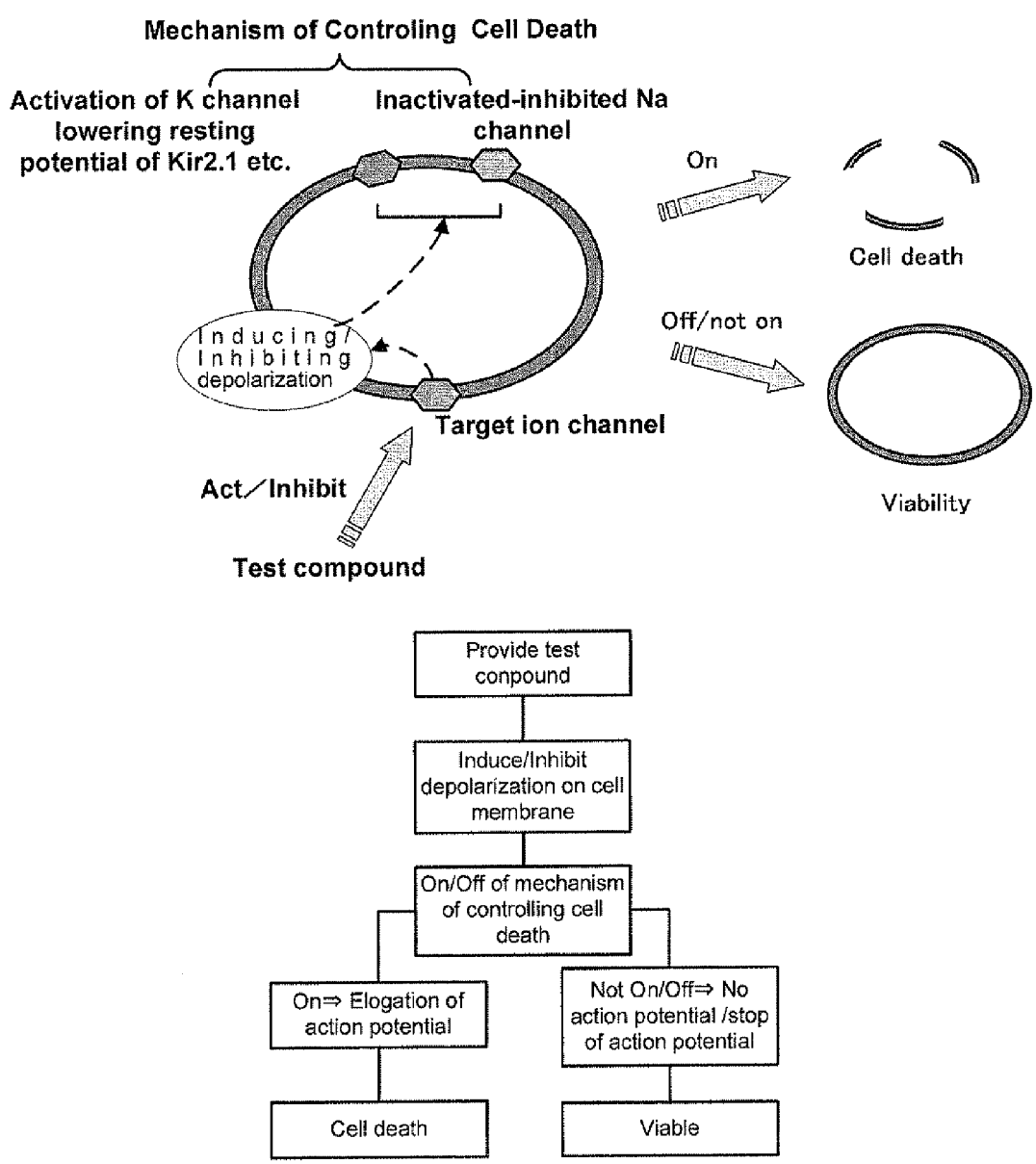
FIG. 1 is a drawing showing an overview of an example of the screening method disclosed in the present description.

An example of an overview of detection of the action of a test compound on a target ion channel according to this mechanism for controlling cell death is shown in FIG. 1. As shown in FIG. 1, when a test compound is supplied to the present screening material in the form of cells provided with an Na ion channel for which inactivation has been inhibited and in which a K ion channel that makes resting potential deeper has been activated, the action of the test compound on the target ion channel is expressed as the result of inducing or inhibiting depolarization.

When a test compound has acted on a target ion channel and depolarization is induced, a switch of the mechanism for controlling cell death based on the above-mentioned Na ion channel and K ion channel on the cell membrane of the present screening material is switched on, and the present screening material undergoes cell death. On the other hand, when a test compound acts on a target ion channel and depolarization is inhibited, the switch of the above-mentioned mechanism for controlling cell death is not switched on and remains off, and the present screening material remains viable.

Thus, the present screening material detects the presence or absence of induction of depolarization attributable to the action of a test compound according to whether or not the mechanism for controlling cell death is switched on or off, or in other words, according to the presence or absence of a sustained action potential that leads to cell death or cell viability. As a result, the action of a test compound on a target ion channel can be detected according to cell viability or death simply without measuring changes in membrane potential.

Since detection of cell viability or death is easier and more precise in comparison with electrical detection in the form of simply detecting cell membrane potential or measuring membrane current, and is suitable for simultaneous evaluation of a large number of specimens, throughput is high. In addition, the procedure is simple and measurement accuracy can be ensured. This type of screening method is also preferable for primary screening for compounds that target ion channels. The following provides a detailed explanation of various embodiments of the disclosure of the present description.

(Screening Material)

The screening material disclosed in the present description comprises cells that retain a first DNA that encodes a voltage-dependent Na ion channel for which inactivation has been inhibited, and in which a K channel, such as an inwardly rectifying K ion channel, for which the resting potential becomes deeper in the negative direction, is activated, and for which cell death is avoided by the inflow of Na ions into the cells. In the following descriptions, these cells are referred to as screening cells.

The present screening material may contain only the screening cells or may also contain a culturing material or additive and the like that allows viability or is suitable for viability of the screening cells in addition to the screening cells. Examples of these culturing materials include ordinary media as well as buffers, antibiotics and the like.

(Inactivation-Inhibited Voltage-Dependent Na Ion Channel)

The screening cells retain a first DNA that encodes a voltage-dependent Na ion channel for which inactivation has been inhibited. The screening cells expressed this Na ion channel. Here, the voltage-dependent Na ion channel refers to a protein on a cell membrane that mediates passive diffusion of Na ions by opening dependent on the membrane potential of the cell. There are no particular limitations on the voltage-dependent Na ion channel used in the present description, and although various types of known voltage-dependent Na ion channels can be used, it is preferably an Nav 1.5 channel. The Nav 1.5 channel is distributed in myocardial cells, and is thought to be involved in the generation of action potential and the conduction of excitation.

A voltage-dependent Na ion channel loses Na ion permeability (is inactivated) due to the action of a inactivation mechanism after a gate opens and Na ion permeability is demonstrated dependent on membrane potential. In contrast, a voltage-dependent Na ion channel for which inactivation has been inhibited is such that this inactivation mechanism has been suppressed (lost). Namely, an inactivation-inhibited voltage-dependent Na ion channel refers to a Na ion channel in which this inactivation does not occur after a gate opens and ion permeability is demonstrated dependent on membrane potential. In an inactivation-inhibited voltage-dependent Na ion channel, although the channel opens and a state able to be mediated by passive diffusion of Na ions is adopted when depolarization is induced in the membrane and the ion channel per se is activated, since inactivation of the ion channel per se is inhibited, the channel is maintained in an open state. As a result, in an inactivation-inhibited voltage-dependent Na ion channel, once it has been subjected to stimulation and an action potential is generated, inactivation of the channel is delayed and the action potential is sustained for a longer period of time than the native voltage-dependent Na ion channel.

In addition, an inactivation-inhibited Na ion channel is either constantly partly activated or easily activated at a comparatively deep resting membrane potential (or in other words, has a so-called large window current). Thus, in cells expressing an inactivation-inhibited Na ion channel, excess inflow of Na ions can be prevented only in the case the resting membrane potential is held to a sufficiently deep negative potential. In cells that have adequately expressed an inactivation-inhibited voltage-dependent Na ion channel, Na ion channel activity is easily increased by depolarization, and action potential or depolarization is maintained for about 1 minute or more, preferably 2 minutes or more, more preferably 3 minutes or more, and even more preferably 5 minutes or more. Consequently, excess inflow of Na into the cells occurs and causes the cells to die.

This inhibition of inactivation can be suitably realized by inserting an amino acid mutation into the amino acid sequence of a voltage-dependent Na ion channel. Several specific techniques have been disclosed for inhibiting inactivation of the Nav 1.5 channel. Examples of reported techniques include modifying an IFM motif (A. O. Grant et al., Biophys. J., Vol. 79, pp. 3019-3035, 2000), mutation of asparagine at position 406 to glutamic acid, arginine or lysine (M. M. McNulty et al., Mol. Pharmacol., Vol. 70, pp. 1514-1523, 2006), deletion of a linker site containing an IFM motif that connects domains III and IV (D. E. Patton et al., Proc. Natl. Acad. Sci. USA, Vol. 89, pp. 10905-10909, 1992; West J. W. et al., Proc. Natl. Acad. Sci. USA, Vol. 89, pp. 10910-10914, 1992), and mutation of an amino acid of segment 4 of domain IV (L. Q. Chen et al., J. Gen. Physiol., Vol. 108, pp. 549-556, 1996). Insertion of a mutation into an amino acid sequence can be suitably carried out by a person with ordinary skill in the art based on these documents and common general technical knowledge.

The screening cells expressably retain a first DNA that encodes this mutant protein in the form of that mutant. The screening cells may constantly or transiently express the mutant, namely the inactivation-inhibited voltage-dependent Na ion channel. In other words, the first DNA may be incorporated in a chromosome so as to be transmitted to a daughter cell, or may be incorporated in a plasmid that is autonomously amplified outside a chromosome and is not necessarily transmitted to a daughter cell. The first DNA is preferably linked under the control of a constantly active promoter (constitutive promoter). These screening cells can be suitably acquired as constantly expressing cells or transiently expressing cells by constructing an expression vector and the like containing the first DNA and then transforming a host of the screening cells by inserting therein based on genetic engineering technology and transformant production technology commonly known among persons with ordinary skill in the art.

Furthermore, in the case the voltage-dependent Na ion channel is composed of two or more subunits, and when subunits containing mutations effective for inactivation only constitute a portion of the entirety thereof, DNA respectively encoding those subunits can be expressed in the screening cells in the form of at least one first DNA, or DNA encoding these subunits may be respectively and expressably retained in the form of the first DNA so that other subunits composing the Na ion channel are simultaneously co-expressed. Moreover, if there are enzymes or other proteins required for the expressed inactivation-inhibited voltage-dependent Na ion channel to function more effectively, these proteins may also be suitably expressed.

(Activation of K Ion Channel)

In the screening cells, a K ion channel is activated so that the resting membrane potential becomes deeper in the negative direction, or in other words, so that the negative potential increases. Namely, the inflow of K ions into the cells is promoted. When the above-mentioned first DNA is retained and an Na ion channel mutation (inactivation-inhibited membrane potential-dependent Na ion channel) is expressed and activated, a state results in which an excess of Na ions flow into the cells due to a concentration difference between Na ions inside and outside the cells, ultimately resulting in the intracellular Na ion concentration increasing and the cells dying. It is necessary that the cells are viable until the cell death mechanism is induced in order to allow the cells to function as screening cells. Therefore, the K ion channel is activated so as to promote the inflow of K ions into the cells in order to deepen (lower) the resting membrane potential. When the K ion channel is activated in this manner, the resting membrane potential can be set deeper in the negative direction than normal.

The resting membrane potential is preferably deepened in the negative direction to a degree that does not affect cell viability. The membrane potential is preferably −50 mV, more preferably −60 mV, even more preferably about −70 mV and still more preferably about −80 mV.

A state in which the K ion channel is activated so that the resting membrane potential becomes deeper in the negative direction refers to, for example, a state in which an inwardly rectifying K ion channel (Kir), 4-pass transmembrane or 2-pore K ion channel or tandem pore domain K ion channel and the like is activated. There are various types of 4-pass transmembrane and 2-pore K ion channels having different properties, and are classified into such types as TWIK, TERK, TASK, TALK, THIK and TRESK. Since these channels are not dependent on potential or time, they function as leak channels. The properties of these leak channels enable them to function to fix the resting membrane potential of cells.

Although there are no particular limitations on the inwardly rectifying K ion channel, examples include various types of Kir 2.x channels such as Kir 2.1, 2.2, 2.3 and 2.4 channels. The Kir 2.1 channel is an inwardly rectifying $K^+$ channel having a two-pass transmembrane structure. This channel is not dependent on voltage and has the property to make membrane potential approaching the K+ equilibrium potential. This channel is expressed in nerves, heart and skeletal muscle, and carries out formation of resting membrane potential along with its stabilization and maintenance. Another example is Kir 2.2. Although Kir 22 is also an inwardly rectifying K ion channel in the same manner as Kir 2.1, it has more potent inward rectification than Kir 2.1. It is expressed with Kir 2.1 in heart, brain and skeletal muscle, and plays a leading role among other inwardly rectifying K ion channels in human vascular endothelial cells.

The Kir 2.x ion channels are described in such publications as Circ. Res. 2004, 94, 1332-1339 and Am. J. Physiol. Cell Physiol. 2005, 289, C1134-C1144. Examples of base sequences encoding human-derived Kir 2.x channels include Kir 2.1 (GenBank Accession No. U12507, NM_00891.2), Kir 2.2 (GenBank Accession No. AB074970, NM_021012 (Human KCNJ12)), Kir 2.3 (GenBank Accession No. U07364, U24056) and Kir 2.4 (GenBank Accession No. AF081466.1).

Similarly, another example is GIRK (Kir 3). GIRK (Kir 3) is an inwardly rectifying K ion channel which, differing from Kir 2, is activated by G protein. Subunits thereof are tissue-specific, and form heterogeneous tetramers composed of Kir 3.1 and Kir 3.4 in the heart or Kir 3.1 and Kir 3.2 in the central nervous system. They are normally not activated, and are only activated by agonist stimulation. However, these channels have been reported to be constantly kept open by mutating amino acids of the transmembrane helix that forms channel pores in an experiment using *Xenopus oocytes* (J. Biol. Chem., 2003, Vol. 278, No. 50, pp. 50654-50663). On the basis of this finding, the use of this mutant is thought to allow the formation of a deep resting membrane potential in the same manner as Kir 2.1. Examples of base sequences that encode human-derived Kir 3.x channels include Kir 3.1 (GenBank Accession No. NM_002239.2), Kir 3.2 (GenBank Accession No. NM_002240.2), Kir 3.3 (GenBank Accession No. NM_004983.2) and Kir 3.4 (GenBank Accession No. NM_000890.3).

Moreover, another example is the $K_{ATP}$ (Kir 6) channel. The $K_{ATP}$ channel is an inwardly rectifying K ion channel that is inhibited by ATP and activated by ADP. The $K_{ATP}$ channel controls cell excitability corresponding to the metabolic state of the cells. The $K_{ATP}$ channel is a heterogeneous octomer composed of four $K_{ATP}$ channels and four sulfonylurea receptors (SUR). Although the $K_{ATP}$ channel alone does not have a function, the $K_{ATP}$ channel alone has been reported to have function by deleting the C terminal (EMBO J., Vol. 17, No. 12, pp. 3290-3296, 1998). In addition, this deletion variant can be made to be constantly activated by decreasing ATP sensitivity by subjecting to further mutation. The use of this mutant also enables the formation of a deep resting membrane potential. Examples of base sequences encoding human-derived Kir 6.x channels include Kir 6.1 (GenBank Accession No. NM_004982.2) and Kir 6.2 (GenBank Accession No. NM_001166290.1).

In addition, known examples of 4-pass transmembrane and 2-pore K ion channels include the THIK channel (in which membrane potential becomes deeper when expressed in HEK293 cells (V. A. Campanucci et al., Neuroscience, Vol. 135, pp. 1087-1094, 2005)), the TASK2 channel (in which resting membrane potential becomes deeper when expressed in *Xenopus oocytes* (C. Kindler et al., J. Pharmacol. Exp. Ther., Vol. 306, pp. 84-92, 2003)), and the Kv ion channel (in which resting membrane potential of the Kv ion channel becomes deeper in smooth muscle tissue (S. S. McDaniel et al., J. Appl. Physiol., Vol. 91, pp. 2322-2333, 2001)).

2-pore K ion channels are classified into their respective subfamilies consisting of TWIK, TREK, TASK, TALK, THIK and TRESK. The TWIK subfamily includes the TWIK-1 and TWIK-2 channels (Cell. Biochem. Biophys. (2007), 47, 209-256). TWIK channels are present in numerous tissues in humans. Examples of human-derived TWIK ion channels include TWIK-1 (GenBank Accession No. NM_002245.3) and TWIK-2 (GenBank Accession No. NM_004823.1).

The TREK subfamily includes the TREK-1, TREK-2 and TRAAK channels. Examples of human-derived TREK ion channels include TREK-1 (GenBank Accession No. NM_014217.3), TREK-2 (GenBank Accession No. NM_138317.2) and TRAAK (GenBank Accession No. NM_033310.2).

The TASK subfamily includes the TASK-1, TASK-3 and TASK-5 channels. Examples of human-derived TASK ion channels include TASK-1 (GenBank Accession No. NM_002246.2), TASK-3 (GenBank Accession No. NM_016601.2) and TASK-5 (GenBank Accession No. NM_022358.3).

The TALK subfamily includes the TALK-1, TALK-2 and TASK-2 channels. Examples of human-derived TALK ion channels include TALK-1 (GenBank Accession No. NM_001135106.1), TALK-2 (GenBank Accession No. NM_001135111.1) and TASK-2 (GenBank Accession No. NM_003740.3).

The THIK subfamily includes the THIK-1 and THIK-2 channels. Examples of human-derived THIK ion channels include THIK-1 (GenBank Accession No. NM_022054.2) and THIK-2 (GenBank Accession No. NM_022055.1).

Examples of the TRESK subfamily include TRESK (GenBank Accession No. NM_181840.1).

In the present screening cells, one or more of these K ion channels can be suitably combined for the purpose of deepening resting membrane potential.

The screening cells in the state in which a K ion channel has been activated so as to deepen resting membrane potential in the negative direction preferably expressably retain the K ion channel protein by using a second DNA that encodes that protein in the form of exogenous DNA. The screening cells may constantly or transiently express the K ion channel. Namely, the second DNA may be incorporated in a chromosome so as to be transmitted to a daughter cell, or may be incorporated in a plasmid that is autonomously amplified outside a chromosome and is not necessarily transmitted to a daughter cell. The second DNA is preferably linked under the control of a constantly active promoter (constitutive promoter). These screening cells can be suitably acquired as constantly expressing cells or transiently expressing cells by constructing an expression vector and the like containing the second DNA and then transforming a host of the screening cells by inserting therein based on genetic engineering technology and transformant production technology commonly known among persons with ordinary skill in the art.

Furthermore, in the case the activated K ion channel is composed of two or more different subunits (which may be subunits of different K ion channels), DNA respectively encoding those subunits is preferably expressed in the screening cells in the form of at least one second DNA. Moreover, in the case there are enzymes or other proteins required for the expressed K ion channel to function effectively, these proteins may also be co-expressed. In that case, DNA encoding these other proteins may be expressably retained. Furthermore, examples of other proteins include G protein in the case, for example, the K ion channel is a G protein-coupled K ion channel.

As a result of the screening cells having a inactivation-inhibited voltage-dependent Na ion channel on a biomembrane such as a cell membrane, and a K ion channel simultaneously acting so as to lower (deepen) resting membrane potential, or in other words, an inwardly rectifying K ion channel and the like acting on the cell membrane, even if the screening cells have an inactivation-inhibited mutant voltage-dependent Na ion channel, cell death due to inflow of Na ions is avoided until depolarization is induced. Namely, a mechanism for inducing cell death, which waits for depolarization to be induced in the cell membrane of the screening cells, is in a standby state.

The screening cells can also be used as host cells for expressing DNA encoding a new target ion channel by gene insertion.

(Target Ion Channel)

There are no particular limitations on the target ion channel in the screening cells, and one or more target ion channels can be suitably selected from known or novel ion channels. Furthermore, an ion channel refers a protein that passes through a biomembrane such as an animal or plant cell membrane or inner membrane and passively allows the permeation of specific ions. Examples of ions include Na ions, K ions, Ca ions and Cl ions. Examples of ion channels include voltage-dependent channels, ligand-dependent channels, mechanical stimulation-dependent channels, temperature-dependent channels, leak channels and phosphorylation-dependent channels depending on the manner of control of the opening and closing thereof. According to the disclosure of the present description, since action (activation or inhibition) on a target ion channel can be detected according to the viability or death of the screening cells, a wide range of ion channels in general can be used as target ion channels. Furthermore, in the present description, an ion channel is referred to regardless of the manner of control of the opening and closing thereof; whether it is a voltage-dependent ion channel or ligand-dependent ion channel and the like. In addition, ion channels include transporters, ion exchangers (such as Na—Ca exchangers) and ion pumps (Na—K pumps) of biomembranes including cell membranes and nuclear membranes engaged in voltage-generating ion transport as well as other intracellular organelle membranes and the like. Screening cells for prevention or treatment of diseases related to a target ion channel are provided by selecting the target ion channel in the screening cells.

A first example of a target ion channel consists of various types of ion channel-integrated drug receptors. Examples of these receptors include nicotinic acetylcholine receptors, ion channel-type ATP receptors (P2x receptors), ion channel-type glutamate receptors, ion channel-type GABA$_A$ receptors, ion channel-type glycine receptors and type 3 serotonin receptors. In addition, other examples include various types of transient receptor potential (TRP) channels (non-selective cation channels). Other examples include store-operated Ca ion channels such as Orai channels and Stim protein. In addition, other examples of target ion channels include various types of voltage-dependent ion channels. Examples thereof include all voltage-dependent Ca ion channels, all voltage-dependent K ion channels (including HERO channels), all voltage-dependent Na ion channels and all voltage-dependent Cl ion channels. Furthermore, other examples include ligand-dependent Ca ion channels, Na ion channels, proton ion channels, K ion channels and Cl ion channels. Moreover, additional examples include all ion channels that open and close by sensing a stimulus such as voltage potential, temperature, pH or tension.

Ion channels intimately related to a disease or symptoms are preferable for the target ion channel. Examples of such Na ion channels include Nav1.1 to 1.3 and Nav 1.5 to 1.9 ion channels. These ion channels are related to epilepsy, neuropathic pain, arrhythmia and other types of pains, and can be used to screen for drugs used to treat or prevent these conditions. In addition, examples of Ca ion channels include Cav 1.1, 1.2, 1.3, 1.4, 2.1, 2.2, 2.3, 3.1, 3.2 and 3.3 ion channels. These ion channels are related to cardiovascular disease, Alzheimer's disease, pain, epilepsy and hypertension, and can be used to screen for drugs used to treat or prevent these conditions. Examples of K ion channels include Kv 1.1 to 1.5, Kv 3.2, Kv 4.3, Kv. 7.1 to 7.5, Kv 10.1, Kv 11.1 (including hERG) and Kv 12.1 to 12.3 ion channels. These ion channels are related to multiple sclerosis, autoimmune diseases, pain, atrial fibrillation, diabetes, epilepsy, neuralgia, Alzheimer's disease, urinary incontinence, arrhythmia and cancer, and can be used to screen for drugs used to treat or prevent these conditions. In addition, examples of Cl ion channels include CLC-1 to 7, -Ka and Kb ion channels, are related to hypertension, and can be used to screen for drugs used to prevent or treat this condition.

In particular, an hERG K ion channel is preferable for the target ion channel. This ion channel is one of the voltage-dependent K ion channels that has a 6-pass transmembrane structure and forms a tetramer. One of the differences between this K ion channel and other voltage-dependent K ion channels is that this K ion channel demonstrates inward rectification. This is attributable to the extremely rapid occurrence of C-type inactivation. This K ion channel also acts strongly in the repolarization phase, which is the third phase of the action potential of the heart. This K ion channel is known to be involved in arrhythmia, since it causes hyperpolarization in the repolarization phase of cardiac action potentials, and also in cancer as well. Since highly fatal long QT syndrome is induced when hERG channels are inhibited, currently all types of drug candidate compounds are required to be assessed for arrhythmia-causing action attributable to cardiotoxicity stemming from inhibitory action on hERG K ion channels. Consequently, screening cells having an hERG K ion channel for the target ion channel are highly useful. In the case of expressing an hERG K ion channel in the screening cells, since an action potential generated by an electrical stimulus, for example, is shortened, cell death is unlikely. By adding a compound that is known to have or suspected to have an inhibitory action on hERG K ion channels, cell death occurs more easily in the screening cells dependent on the degree of that inhibition, thereby making it possible to quantitatively evaluate inhibitory effects on hERG K ion channels. An example of hERG is GenBank Accession No. NM_000238.2.

Any screening cells can be used for screening provided they express a target ion channel. The screening cells used for screening preferably specifically express or highly express a target ion channel. This is for the purpose of screening having more favorable accuracy and sensitivity. Since ion channels are frequently distributed in specific cells, cells highly expressing an ion channel to be targeted in advance can be selected as parent cells of the screening cells. However, in order to stably express a target ion channel in screening cells ex vitro, the screening cells retain and express DNA encoding the target ion channel (third DNA). In addition, the screening cells may constantly or transiently express a target ion channel. Namely, the third DNA may be incorporated in a chromosome so as to be transmitted to a daughter cell, or may be incorporated in a plasmid that is autonomously amplified outside a chromosome and is not necessarily transmitted to a daughter cell.

The third DNA is preferably linked under the control of a constantly acting promoter (constitutive promoter). These screening cells can be suitably acquired as constantly expressing cells or transiently expressing cells by constructing an expression vector and the like containing the third DNA and then transforming a host of the screening cells by inserting therein based on genetic engineering technology and transformant production technology commonly known among persons with ordinary skill in the art.

Furthermore, in the case the target ion channel to be expressed is composed of two or more different subunits (which may be subunits of different ion channels), DNA respectively encoding those subunits is preferably expressed in the screening cells in the form of at least one third DNA. Moreover, in the case there are enzymes or other proteins required for the expressed target ion channel to function effectively, these proteins may also be co-expressed. In that case, DNA encoding these other proteins may be expressably retained. Furthermore, examples of other proteins include various types of receptor proteins, GTP-binding protein and phosphorylase.

There are no particular limitations on host cells of the screening cells provided they can be used for screening, and various types of animal and plant cells can be used. Examples of animal cells include mammalian cells and insect cells, although there are no particular limitations thereon. In the case the host cells are cells other than human cells such as bovine, porcine, equine, avian, canine or feline cells, screening cells of drugs can be obtained for preventing or treating diseases in these animals. In addition, in the case of using insect cells for the host, screening cells can be acquired that can be used to screen agricultural chemicals and the like targeted for use against insects. In addition, when the host cells are plant cells, screening cells can be acquired that can be used to screen agricultural chemicals and the like. Examples of animal cells that are typically used include human embryonic kidney cells (HEK cells), African green monkey cells (COS cells), Chinese hamster ovary cells (CHO cells), baby hamster kidney cells (BHK cells) and *Zenopus* oocytes.

(Screening Method)

The screening method disclosed in the present description can be provided with a step of detecting the action of a test compound on a target ion channel by using the viability or death of screening cells as an indicator using screening cells of the screening material disclosed in the present description. According to the present screening method, the use of the screening cells disclosed in the present description makes it possible to detect the action of a test compound on a target ion channel by using the viability or death of the screening cells as an indicator. Consequently, a large number of specimens can be evaluated simultaneously both easily and with high efficiency. In addition, since special procedures and equipment are not required, screening costs can be reduced without lowering accuracy inherent to the procedure.

The screening method disclosed in the present description can be used to screen for drugs used to prevent or treat diseases or symptoms involving a target ion channel by using screening cells targeting various types of ion channels as previously explained. When carrying out screening, one or more test compounds can be supplied to the screening cells. The action of a test compound may be detected using a single test compound, or the combined action or synergistic action of two or more test compounds may be detected using those compounds. In the detection of the action on a target ion channel based on the viability or death of the screening cells, viability or death of the screening cells in the case of not supplying a test compound can be used as a control. Alternatively, a compound with a known action on a target ion channel can be used as a control. The presence or absence of the action of a test compound on a target ion channel, or the degree of that action, can be detected by comparing with such a control.

There are no particular limitations on the test compound. In addition to low molecular weight compounds, the test compound may be a protein, peptide, nucleic acid (DNA or RNA) such as an oligonucleotide or polyoligonucleotide, oligosaccharide, polysaccharide or lipid.

Various types of stimuli may be imparted to the screening cells as necessary in addition to a test compound. This is because action may be promoted or inhibited by combining with these stimuli. In addition, the action on a target ion channel that is activated or inactivated in the presence of a stimulus can also be evaluated. Examples of such stimuli include temperature changes (high temperature or low temperature), pH changes, changes in $O_2/CO_2$ concentration and changes in osmotic pressure.

In addition, as will be subsequently described, there are cases in which it is necessary to induce depolarization of the cell membrane of the screening cells in the detection step. In this case, a stimulus that is unlikely to affect the test compound such as an electrical stimulus is used preferably.

In the detection of the action of a test compound on a target ion channel using cell death of the screening cells as an indicator, the indicator is not limited to a one-in-two choice in terms of the viability or death of the screening cells, but rather includes the use of the ratio of cell death (or in other words, the ratio of viable cells) as an indicator. By using the ratio of cell death as an indicator, the potency or degree of an action or sensitivity and the like can also be evaluated. Various types of known techniques can be employed without any particular limitations for the method used to detect cell death of the screening cells (or viability of the screening cells). Examples of such methods include various techniques such as the MTT method based on cell staining, nuclear staining or enzyme activity. These techniques can be suitably selected in consideration of accuracy and efficiency. In addition, cell death can also be detected by detecting a sustained action potential leading up to cell death. Namely, the duration of an action potential like that which leads to cell death may be detected. The sustained state of this action potential may be detected by conventional electrical detection of membrane potential or by fluorescence membrane potential detection or the use of membrane potential-sensitive dyes.

In the screening method disclosed in the present description, the mode of the screening method is suitably selected corresponding to the type of target ion channel. More specifically, the mode of the screening method is suitably selected corresponding to the control method or function of the target ion channel. For example, the presence or absence of a stimulus or the type of stimulus for activating (or inactivating) a target ion channel is selected corresponding to the control method of the target ion channel (such as whether it is voltage-dependent, ligand-dependent, mechanical stimulation-dependent, temperature-dependent, a leak channel or phosphorylation-dependent and the like). In addition, the evaluation mode that uses cell death as an indicator (such as by activating or inhibiting the target ion channel) is selected corresponding to the function of the target ion channel. For example, in the case the target ion channel is a voltage-dependent ion channel, various types of functions are known to be expressed by activation (activation by a prescribed membrane depolarization). Specific examples thereof include generation of action potential, conduction of excitation (which are associated with Na ion channels), release of neurotransmitters, generation of action potential in nerves and cardiac muscle (which are associated with Ca ion channels), maintaining membrane potential, control of excitation, repolarization of action potential (which are associated with K ion channels), membrane potential repolarization, protein reabsorption, bone matrix absorption and Cl transport (which are associated with Cl ion channels).

For example, when the target ion channel is an ion channel that induces depolarization of a biomembrane such as the cell membrane of screening cells by activation, examples of screening modes used in the detection step are indicated below.

Namely, one example is (1) a step of detecting the action of a test compound on the target ion channel of a screening material in the presence of the test compound by using viability or death of the screening cells as an indicator. More specifically, the viability or death of the screening cells is detected after having imparted the test compound to the screening cells. When promotion of cell death has been detected, the test compound can be determined to be an agonist (activator) having an activating action on the target ion channel.

In addition, when similarly using an ion channel as a target, another example is (2) a step of detecting the action of a test compound by using viability or death of the above-mentioned cells as an indicator in the presence of the test compound and a stimulus that acts on the target ion channel. More specifically, the test compound is preliminarily imparted to the screening cells, and a known agonist of the target ion channel is subsequently added followed by detecting the viability or death of the screening cells. In the case cell death is not detected or cell death is inhibited, the test compound can be determined to be an antagonist (inhibitor) that is inhibitory with respect to the target ion channel.

In addition, when the target ion channel is an ion channel such as a leak channel that inhibits depolarization and/or action potential (promotes hyperpolarization) of the cell membrane of screening cells and the like, an example of the mode of the detection step is indicated below. Namely, the action of a test compound is detected by using viability or death of the screening cells as an indicator in the presence of the test compound and a stimulus that induces depolarization of a biomembrane of the screening cells. In this case, in the presence of the test compound, the target ion channel is constantly activated, and depolarization is inhibited or action potential is inhibited (repolarization is promoted). Consequently, even when a mechanism for controlling cell death is activated by imparting a stimulus such as an electrical stimulus that induces depolarization of the cell membrane of the screening cells, the action potential is neither generated nor prolonged. As a result, the screening cells remain viable. On the other hand, when the test compound and the above-mentioned stimulus are imparted to the screening cells, if cell death of the screening cells is promoted, then the test compound can be determined to be an inhibitor that inhibits the target ion channel.

In addition, when the target ion channel is an ion channel such as an hERG K ion channel that inhibits depolarization and/or action potential (promotes repolarization) of a biomembrane such as the cell membrane of screening cells by activation, an example of the screening mode in the detection step is indicated below. Namely, the action of a test compound is detected by using viability or death of screening cells as an indicator in the presence of the test compound and a stimulus that induces depolarization of the biomembrane of the screening cells. More specifically, when depolarization of the biomembrane has been induced by an electrical stimulus and the like either simultaneous to or following the imparting of the test substance to the screening cells, if cell death of the screening cells is inhibited, then the test compound can be determined to be an agonist that activates the target ion channel. On the other hand, when cell death of the screening cells has been promoted, the test compound can be determined to be an inhibitor that inhibits the target ion channel.

As has been described above, according to the screening method disclosed in the present description, the action of a test compound on a target ion channel can be easily and efficiently detected in various modes by using viability or death of screening cells as an indicator. This screening method is also suitable for screening systems requiring rapid results as well as screening for drugs targeted at ion channels having a difficult chemical structure, and particularly primary screening requiring high throughput.

(Testing Method)

According to the disclosure of the present description, a method for testing a test compound is also provided that is provided with a step of detecting the action of a test compound on a target ion channel by using the viability or death of screening cells as an indicator using screening cells of the screening material disclosed in the present description. According to this testing method, the action of a test compound on a target ion channel (activation or inhibition) can be measured both easily and rapidly. Thus, it is useful as a testing method in the case that a test compound is required to have action of a fixed degree or more. The various types of modes of the screening method disclosed in the present description as previously explained can be used directly in the testing method disclosed in the present description.

(Screening Device)

The screening device disclosed in the present description is a device for screening for a compound having an action on an ion channel, and can be provided with a cell housing unit provided with one or more regions that house cells (cell housing regions), and a measurement unit for measuring cell death of the above-mentioned cells in the above-mentioned one or more regions. According to the screening device disclosed in the present description, since the cell death measurement unit is provided, cell death in the cell housing unit can be detected efficiently. This screening device can use the screening cells disclosed in the present description. Furthermore, various methods can be employed to detect cell death as previously explained in the present screening method.

The cell housing unit can be provided with wells of a known multi-well plate or wells of a similar size thereto for the cell housing regions provided those are able to house a number of cells suitable for measuring cell death. These wells are normally also able to contain a medium so as to be able to incubate the cells. The wells are preferably arranged in the form of an array.

The cell death measurement unit can employ various modes corresponding to the method used to detect cell death. For example, in the case of detecting viable cells or dead cells by supplying one or more drugs, a drug supply unit can be provided that allows the drug to be supplied to the cell housing regions. The drug supply unit is typically a drug injection unit for simultaneously or sequentially supplying a drug to the cell housing regions, while other examples thereof include a drug storage unit for storing a drug, a pump unit for transporting a drug from the drug storage unit and discharging from the drug injection unit, and a control unit for controlling the amount of drug supplied. Among each of these units, the drug injection unit is preferably provided, while each of the other units are suitably provided as necessary.

In addition, the cell death measurement unit, although varying according to the detection method, may be provided with an optical detection unit for electrically or optically detecting cell death of the cells in the cell housing regions. In addition to being provided with a light source, the optical detection unit can normally be provided with a scanner unit and further provided with a control unit for calculating detected signals as light intensity by referring to a control and the like.

Moreover, the cell death measurement unit and/or the screening device can be provided with a storage unit that controls the screening step and stores results, and a control unit provided with the storage unit. Moreover, a display unit can also be provided that displays these steps and results. Moreover, a printer unit can be provided for printing out results.

The screening device can also be provided with a voltage application unit for applying a voltage to one or more of the cell housing regions. As a result of making it possible to impart an electrical stimulus to cells in the cell housing regions, a procedure for imparting an electrical stimulus in the detection step of the screening method can be carried out efficiently. This voltage application unit can be used to activate a mechanism for controlling cell death by imparting an electrical stimulus to the present screening cells in the cell housing regions and inducing depolarization of the cell membrane. The voltage application unit can be provided with electrodes applied to a portion or all of the cell housing regions, and a power source for applying voltage to the electrodes. In addition, the applied voltage is preferably controlled by the previously explained control unit.

(Screening Kit)

The screening kit disclosed in the present description is provided with the screening material disclosed in the present description. According to this kit, screening for a test compound that acts on an ion channel using the present screening cells can be carried out both easily and efficiently. The present kit may also be provided with a reagent for measuring cell death in addition to the present screening material. In addition, the present kit may also be provided with a medium suitable for the screening cells. The present screening kit can be further provided with the screening device disclosed in the present description. The screening cells, screening material and screening device used in the present screening kit are suitably selected and combined from the various types of modes previously explained.

EXAMPLES

Although the following provides an explanation of examples embodying the disclosure of the present description, the disclosure of the present description is not limited thereto.

Example 1

Production of IFM Motif Mutant of Nav 1.5 Channel Inactivation Site

The hydrophobic amino acid sequences Ile-Phe-Met (IFM motif) present in the III-IV linker region that controls inactivation of the Nav 1.5 channel were all mutated to Gln. The amino acid sequence (motif) following mutation is shown below.

hNav 1.5 Amino Acid Sequence (only the region containing IFM targeted for mutation is shown)

```
                                              (SEQ ID NO: 1)
   1470-IDNFNQQKKKLGGQDIFMTEEQKKYYNAMKK-1500
```

(The Underlined Portion of IFM is Mutated to QQQ)

An inactivation-inhibited mutant Nav-QQQ was produced by using pcDNA3.1/Nav1.5, obtained by subcloning human-derived Nav 1.5 (GenBank Accession No.: NM_198056.2) in pcDNA3.1(+) (Invitrogen Corp.) as template, and using the specific PCR primers indicated below and the Quik Change Site-Directed Mutagenesis Kit (Stratagene Corp.). The DNA sequence of the resulting clone was confirmed using the Big Dye Terminator Ver. 3.1 Cycle Sequencing Kit (Applied Biosystems Inc.) and a fluorescent capillary sequencer (ABI Prism 3100 Avent Genetic Analyzer, Applied Biosystems Inc.), and plasmid DNA was purified in large volume using the Hipure Plasmid Maxiprep Kit (Invitrogen Corp.).

```
Primers:
                                              (SEQ ID NO: 2)
   5'-GTTAGGGGGCCAGGACCAACAACAGACAGAGGAGCAGAAG-3'

(SEQ ID NO: 3)
   5'-CTTCTGCTCCTCTGTCTGTTGTTGGTCCTGGCCCCCTAAC-3'
```

Example 2

Cell Culturing and Gene Insertion

Human-derived embryonic kidney cells (HEK293 cells) were purchased from the Health Sciences Research Resource Bank (HSRRB). 10% FBS (Gibco Corp.) was added thereto followed by culturing at 37° C. in 5% $CO_2$ in D-MEM medium (Wako Pure Chemical Industries, Ltd.) containing 100 U/ml penicillin (Wako Pure Chemical Industries, Ltd.) and 100 µg/ml streptomycin (Meiji Seika Kaisha, Ltd.). pcDNA/Kir 2.1, obtained by subcloning human-derived Kir 2.1 (NM_00891.2) in pcDNA3.1(+) (Invitrogen Corp.), was inserted using Lipofectamine 2000 reagent (Invitrogen Corp.) followed by culturing in medium obtained by adding 0.2 mg/ml Zeocin (Invitrogen Corp.) to the above-mentioned D-MEM medium and then cloning Zeocin resistant cells to produce Kir 2.1 constantly expressing cells (HEK-Kir). In addition, the inactivated mutant Nav-QQQ (HEK-Kir-mutated Nav) was inserted into the Kir 2.1 constantly expressing cells using the same method followed by conducting experiments 24 to 72 hours later.

(Electrophysiological Experiment)

Current measurement was carried out using the patch clamp method established by Hamill et al. A glass microelectrode having a tip diameter of about 1 µm was fabricated with a two-stage electrode fabrication machine (PB-7, Narishige Co., Ltd.) from a glass tube containing a filament having an outer diameter of 1.04 µm to 1.08 µm, followed by heat treating under a microscope at a magnification of 500× to smoothen the tip. In the present experiment, an electrode was used in which the electrode resistance was 2 MΩ to 5 MΩ when filled with an electrode internal liquid. A glass slide, in which the cells were bound in a chamber having a volume of about 500 µl and fixed on the stage of an inverted microscope (Nikon TMD), was immobilized and perfused with an external fluid. The composition of the external liquid (normal HEPES buffer) consisted of 137 mM NaCl, 5.9 mM KCl, 2.2 mM $CaCl_2$, 1.2 mM $MgCl_2$, 14 mM glucose and 10 mM HEPES (pH 7.4 as determined with NaOH). The composition of the pipette internal solution consisted of 140 mM KCl, 4 mM $MgCl_2$, 5 mM ATP-2Na, 0.05 mM EGTA and 10 mM HEPES (pH 7.2 as determined with KOH). All of the experiments were carried out at room temperature (23±1° C.). The glass microelectrode was pressed against those cells adhering to the glass slide with a hydraulic micromanipulator (MO-203, Narishige Co., Ltd.), and data was recorded using the voltage clamp method and current clamp method. The measured currents and potentials were amplified using a microcurrent amplifier (EPC-7: Heka Electronik GmbH) and recorded on a computer using an A-D converter (Digdata 1400A: Axon Instruments Inc.). Data was analyzed using Clampfit 10.2 software (Axon Instruments Inc.) and Origin 6.0J (Microcal Software Inc.).

(Measurement of Cell Death)

Three types of cells (HEK, HEK-Kir and HEK-Kir-mutated Nav) were disseminated in a 96-well plate containing 100 µl of D-MEM medium to a concentration of $5 \times 10^3$ cells/well followed by culturing at 37° C. in 5% $CO_2$. One day later, two stimulating silver wire electrodes having a diameter of 0.5 mm were inserted into the culture liquid in each well so that the tips thereof were inserted to a depth of about 2 mm, followed by electrically stimulating at four current strengths of 40 mA, 80 mA, 120 mA and 160 mA (strengths 1 to 4) using a square wave having a stimulating amplitude of 200 ms three times at 3 minute intervals using an electrical stimulation device (Nihon Kohden Corp.). The conditions of electrical stimulation are not necessarily required to be as indicated above, but are only required to be selected so as to be able to reliably generate an action potential. Subsequently, the cells were cultured at 37° C. in 5% $CO_2$, and one day later, 10 µl of MIT reagent (prepared by dissolving to a final concentration of 5 mg/mL with phosphate-buffered saline PBS(–)) was added, the cells were cultured at 37° C. in 5% $CO_2$ for 4 hours and then 100 µl of a lysis solution (20% SDS/50% DMF solution) was added to lyse the cells and dissolve the formazan salt. Moreover, after incubating for 8 hours to 12 hours at 37° C., light absorbance was measured using Multiscan JX (Ver. 1.1, Thermo Labsystems Inc., U.S.A.) at a measuring wavelength of 595 nm and reference wavelength of 650 nm, and used as an indirect indicator of the number of viable cells. However, measurements can also be made by shortening the above-mentioned times of 4 hours and 8 to 12 hours to 2 hours and 3 hours, respectively.

(Results)

1. Functional Analysis of HEK-Kir Cells

Figure 2:
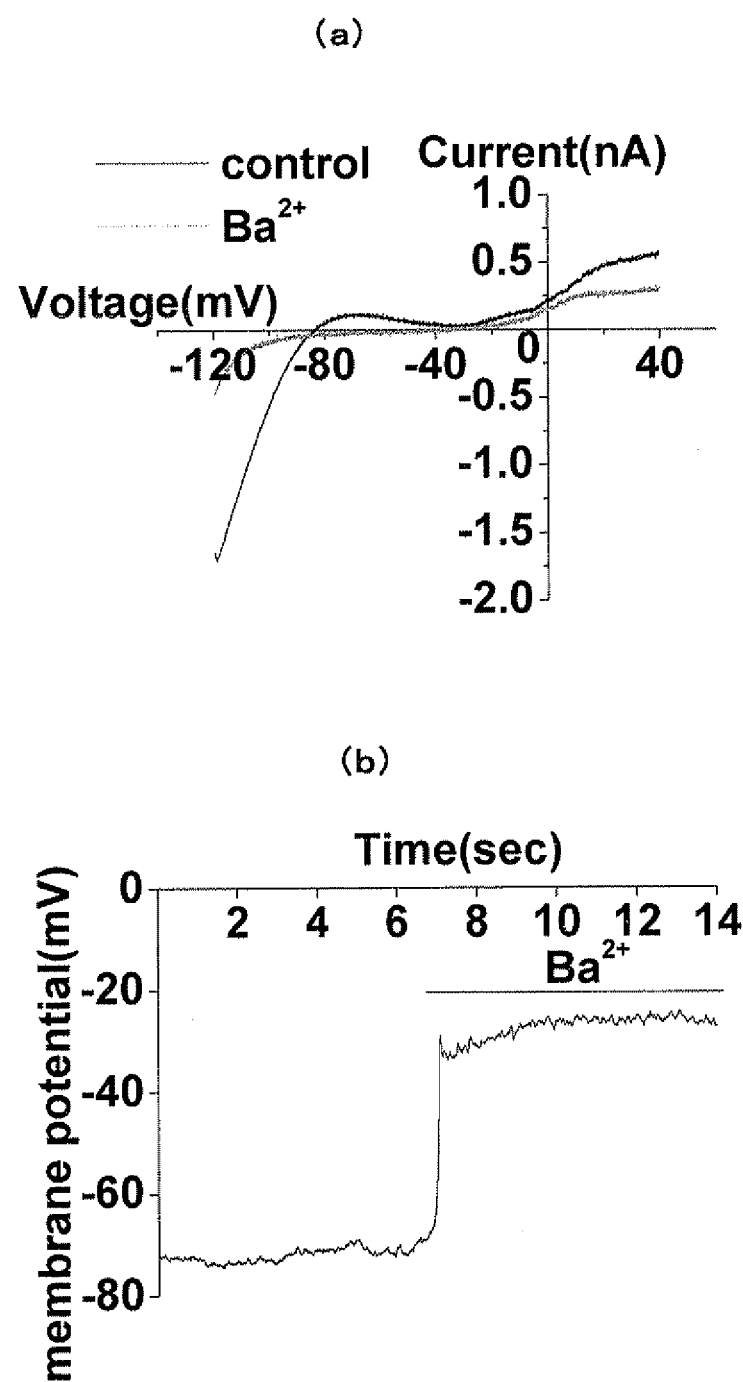
FIG. 2 shows graphs indicating the results of measuring Kir channel current in HEK-Kir cells using the voltage clamp method.

Kir channel current was measured by applying the voltage clamp method to HEK-Kir cells. As a result, as shown in FIG. 2A, inward rectifying property of Kir channel current was observed, and the inward current was inhibited when a selective inhibitor, 100 µM Ba ions were administered. In addition, when membrane potential was measured with the current clamp method, as shown in FIG. 2B, a deep resting membrane potential of about –70 mV was observed, and the resting current potential became shallow due to administration of Ba ions at 100 µM.

2. Inactivation Rate of Wild and Mutant Nav 1.5 Channel Current and Differences in Action Potential Generation Times (Duration)

Figure 3:
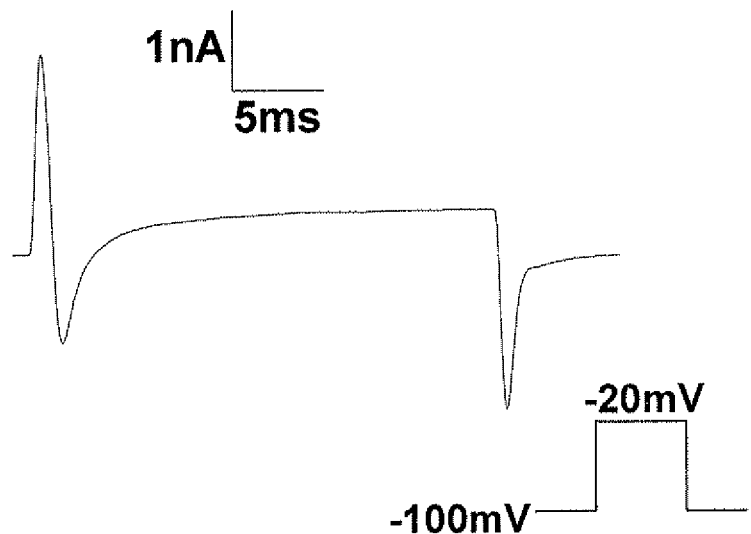
FIG. 3 shows current diagrams indicating the results of measuring Na ion current by transiently expressing wild and mutant Nav 1.5 channels in HEK-Kir cells.
Figure 3:
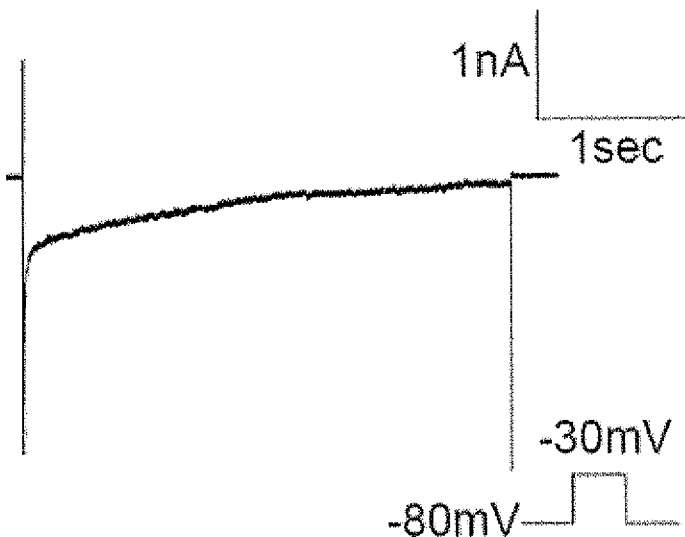
Figure 4:
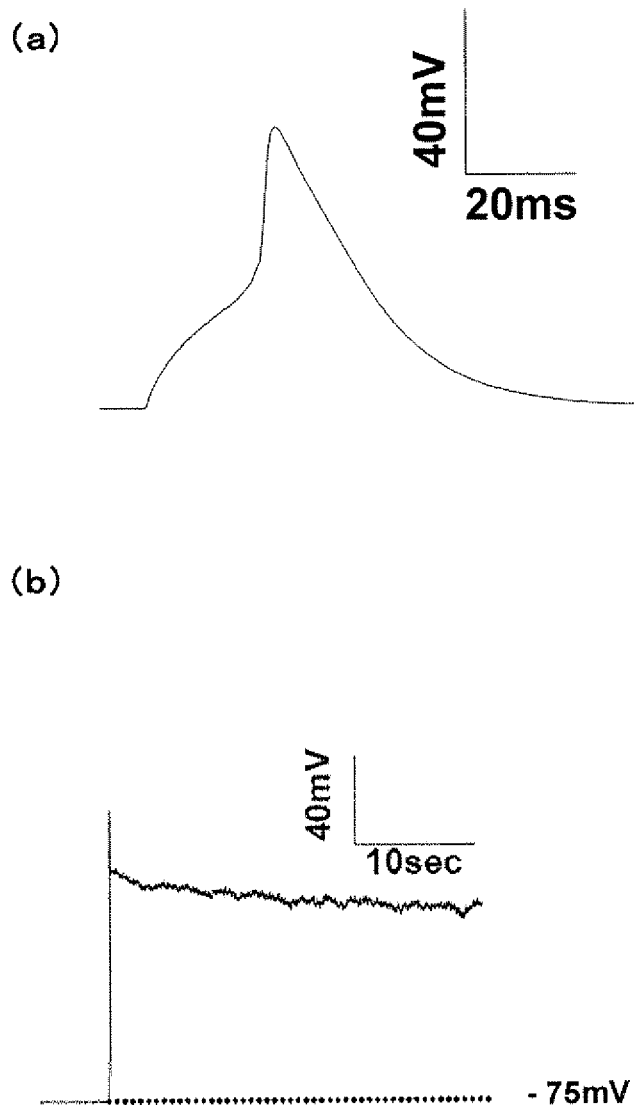
FIG. 4 shows action potential diagrams indicating the generation of action potential by depolarizing electrical stimulation by transiently expressing wild and mutant Nav 1.5 channels in HEK-Kir cells.

Wild and mutant type Nav 1.5 channels were transiently expressed in HEK-Kir cells followed by measurement of Na ion channel current. As a result, as shown in FIG. 3, current was observed for which inactivation of Na ion channel current was extremely slow in the case of the mutant type (FIG. 3B). In addition, when action potential was generated by depolarizing electrical stimulation (300 pA for 10 ms for the wild type and 200 pA for 100 ms for the mutant type) using the same cells, the time during which action potential was generated in the case of the mutant type (FIG. 4B) was determined to be significantly longer. The results are shown in FIG. 4.

3. Changes in Cell Death Attributable to Electrical Stimulation

Figure 5:
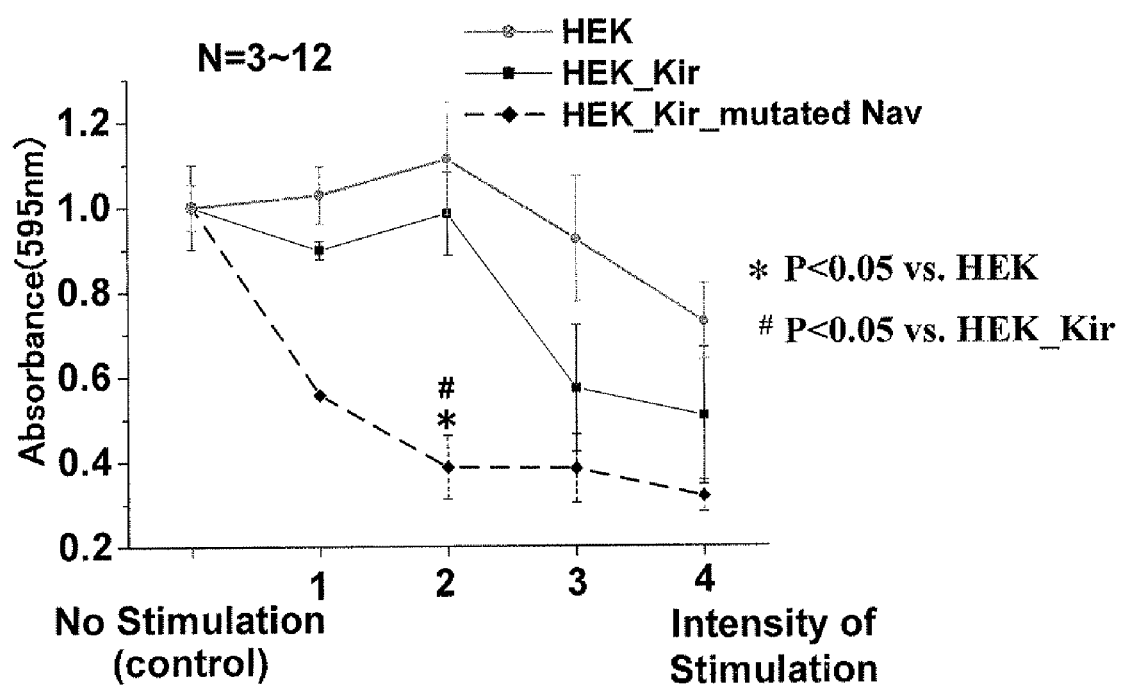
FIG. 5 is a graph indicating the results of measuring changes in cell count by the MIT method by electrically stimulating three types of cells consisting of HEK, HEK-Kir and HEK-Kir-mutated Nay cells; a value of 1 is assigned to the absorbance of control cells that were not stimulated.
Figure 6:
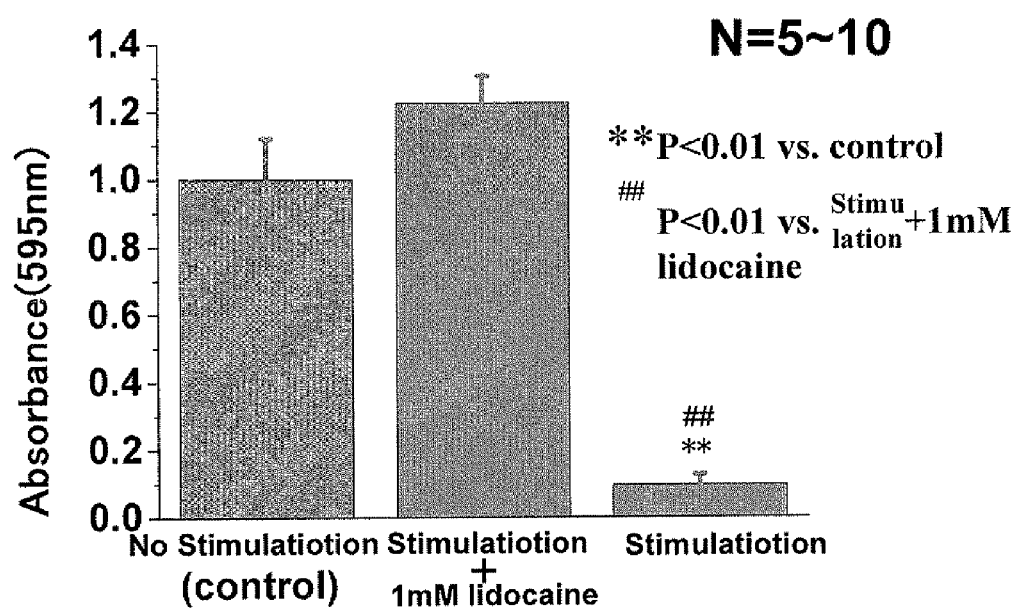
FIG. 6 is a graph indicating the results of administering an Na ion channel inhibitor in the form of lidocaine (Sigma Corp.) to HEK-Kir-mutated Nav cells followed by electrical stimulation; a value of 1 is assigned to the absorbance of control cells that were not stimulated.

It was clearly determined from the results described in section 2 above that an extremely long action potential is generated in the mutant type Nav 1.5 channel. Since there is thought to be the possibility of cell death occurring when the action potential is generated by electrical stimulation, cell death attributable to electrical stimulation was measured. Three types of cells consisting of HEK, HEK-Kir and HEK-Kir-mutated Nav cells were subjected to electrical stimulation followed by measurement of changes in cell count by the MTT method. As shown in FIG. 5, the number of HEK-Kir-mutated Nav cells decreased significantly when subjected to square wave electrical stimulation at 80 mA for 200 ms, three times (at 3 minutes intervals). This indicates that HEK-Kir-mutated Nav cells are highly sensitive to depolarizing stimulation. In addition, an Na ion channel inhibitor, lidocaine (Sigma Corp.) was administered followed by subjecting to electrical stimulation at the same stimulation intensity. As a result, as shown in FIG. 6, the occurrence of cell death was inhibited. On the basis thereof, cell death was determined to occur in HEK-Kir-mutated Nav cells as a result of generating an extremely long action potential, while inhibition of Na ion channels blocked cell death.

Example 3 hERG-HEK cells and hERG-Kir-mutated Nav cells were produced in compliance with Example 2 by subcloning human-derived hERG (NM_000238.2) in pcDNA3.1(+) and inserting into native HEK cells and constantly expressed HEK-Kir-mutated Nav cells, followed by conducting an electrophysiological experiment 24 hours to 72 hours later. The electrophysiological experiment was conducted on the native HEK cells, hERG-HEK cells and hERG-HEK-mutated Nav cells in compliance with Example 2, followed by measurement of hERG channel current and action potential. The hERG K ion channel exhibited inward rectification, and in the case of having been expressed in screening cells, acted to inhibit cell death by shortening the action potential generated by electrical stimulation and the like.

Figure 7:
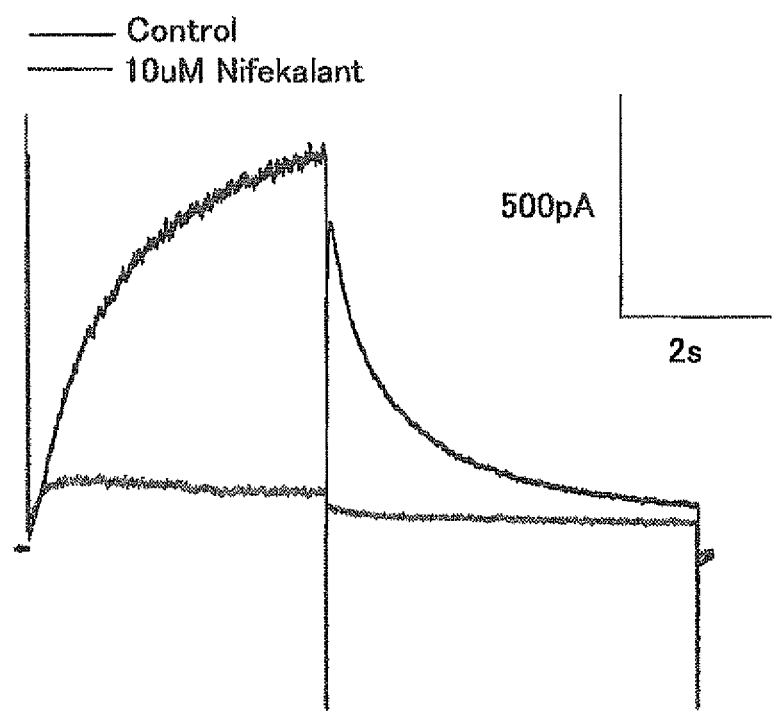
FIG. 7 shows current diagrams before and after administration of nifekalant in the case of having transiently expressed an hERG channel in HEK cells.
Figure 8:
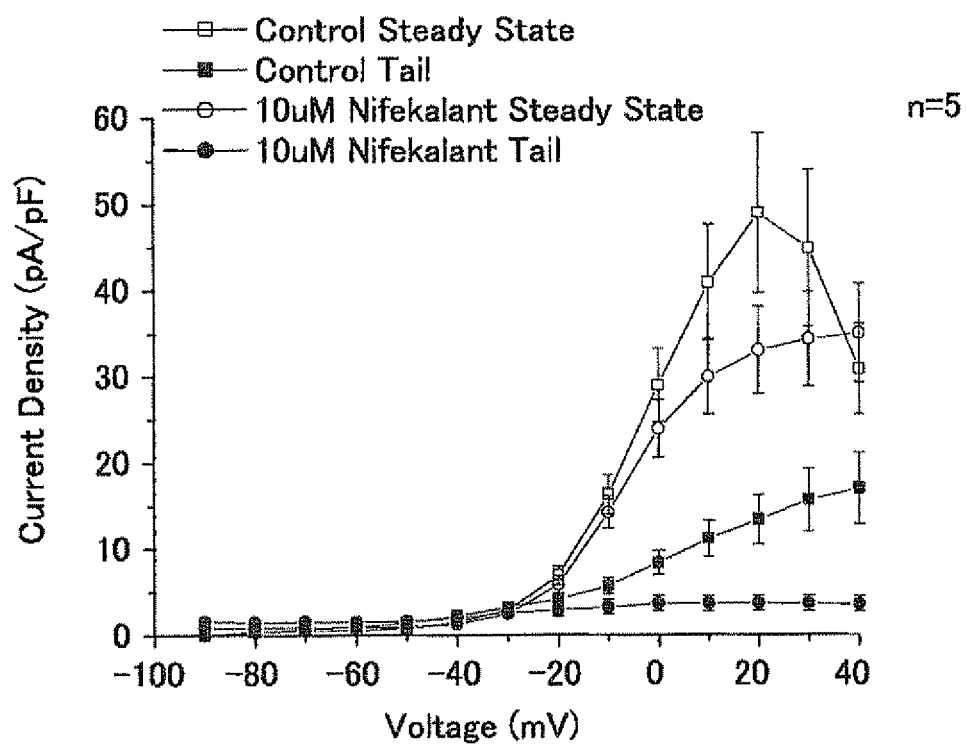
FIG. 8 is a graph indicating current-voltage curves before and after administration of nifekalant in hERG-HEK cells in which an hERG channel was transiently expressed.

An hERG channel inhibitor, nifekalant was administered to hERG-HEK cells, obtained by transiently expressing an hERG channel in native HEK cells, and potential in the cell membrane was measured before and after administration. The current diagrams are shown in FIG. 7, while the current-voltage curves are shown in FIG. 8. As shown in FIGS. 7 and 8, hERG channel current was determined to be inhibited following administration of nifekalant.

In addition, nifekalant was administered to hERG-HEK-Kir mutated Nav cells, obtained by transiently expressing an hERG channel in HEK-Kir-mutated Nav cells, and current of the cell membrane was measured before and after administration. The current diagrams are shown in FIG. 9, action potential drawings generated by depolarizing electrical stimulation are shown in FIG. 10, and action potential times (duration) generated by depolarizing electrical stimulation are summarized in FIG. 11.

Figure 9:
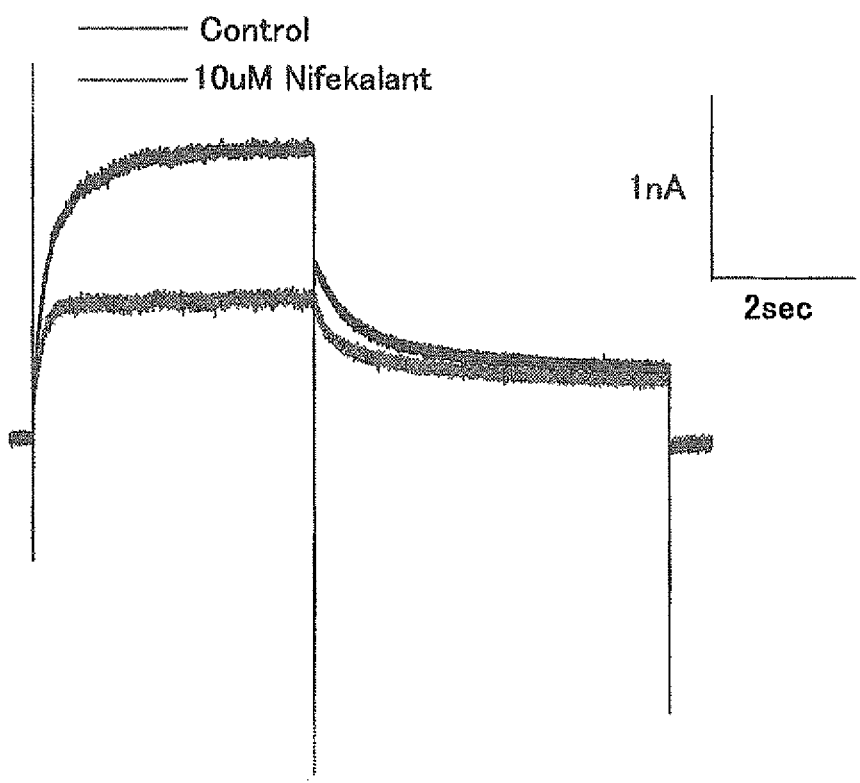
FIG. 9 shows current diagrams before and after administration of nifekalant in hERG-HEK-Kir-mutated Nav cells in which an hERG channel was transiently expressed in Kir-mutated Nav cells.
Figure 10:
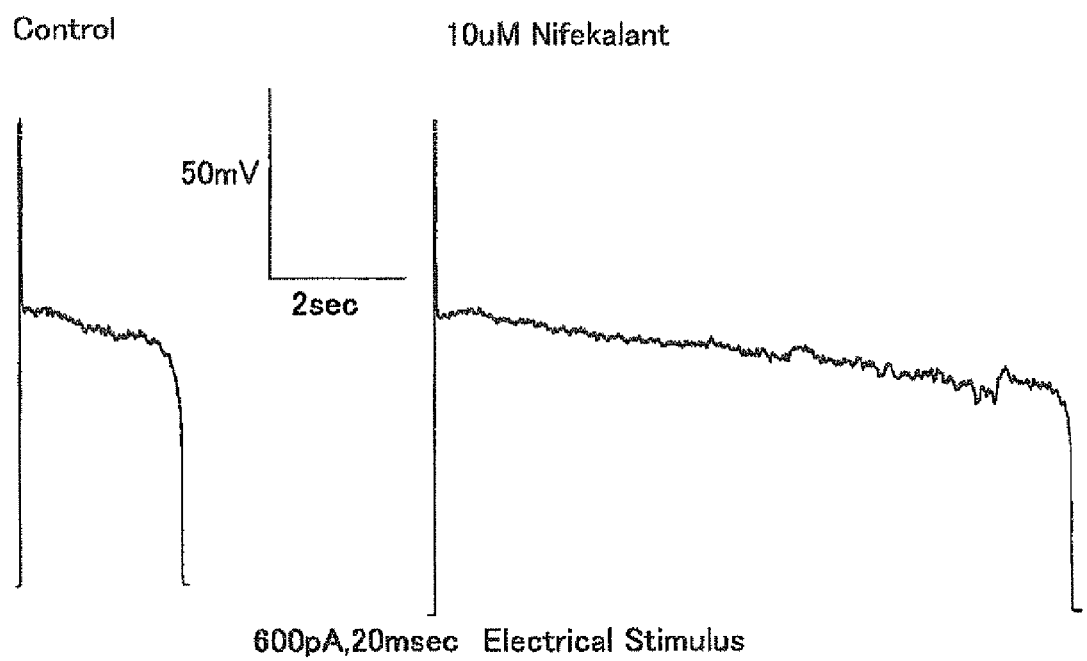
FIG. 10 shows action potential diagrams induced by depolarizing stimulation before and after administration of nifekalant in hERG-HEK-Kir-mutated Nav cells.
Figure 11:
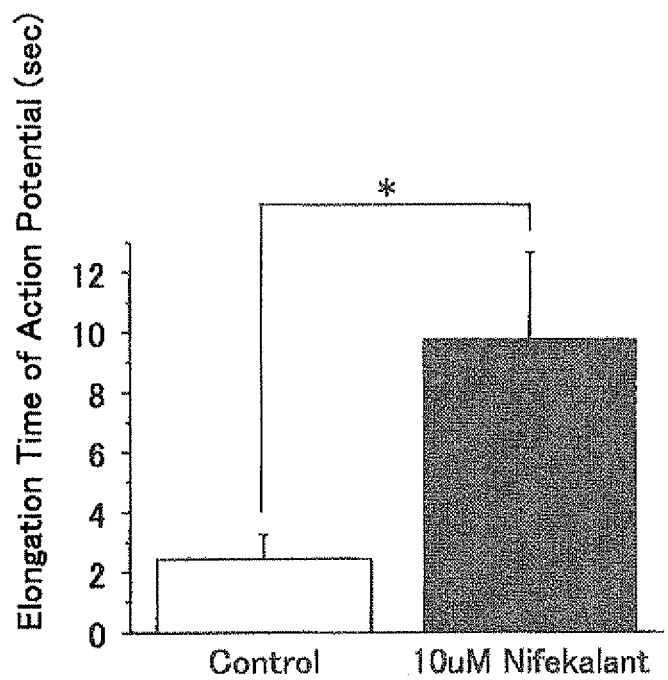
FIG. 11 is a graph indicating action potential times (duration) before and after administration of nifekalant in hERG-HEK-Kir-mutated Nav cells.

As shown in FIGS. 9 to 11, in the case of hERG-HEK-Kir-mutated Nav cells that are provided with a mechanism for controlling cell death and expressed hERG, the duration of the action potential was shortened by hERG when nifekalant was not administered, while the hERG channel was inhibited by administration of nifekalant, and the duration of the action potential was significantly prolonged. On the basis of the above results, when an hERG channel is expressed in HEK-Kir-mutated Nav cells, it was thought that cell death attributable to electrical stimulation is inhibited and that cell death is induced by administration of nifekalant.

Example 4

In the present example, induction of cell death by electrical stimulation and nifekalant was examined in hERG-HEK-Kir-mutated Nav cells. Measurement of cell death was carried out in compliance with Example 2. Furthermore, electrical stimulation was carried out by electrically stimulated three times (at intervals of 3 minutes) with a square wave pulse for 200 ms at 150 mA. The results for induction of cell death by administration of nifekalant are shown in FIG. 12, while a dose-response curve for the dose of nifekalant required to induce cell death is shown in FIG. 13.

Figure 12:
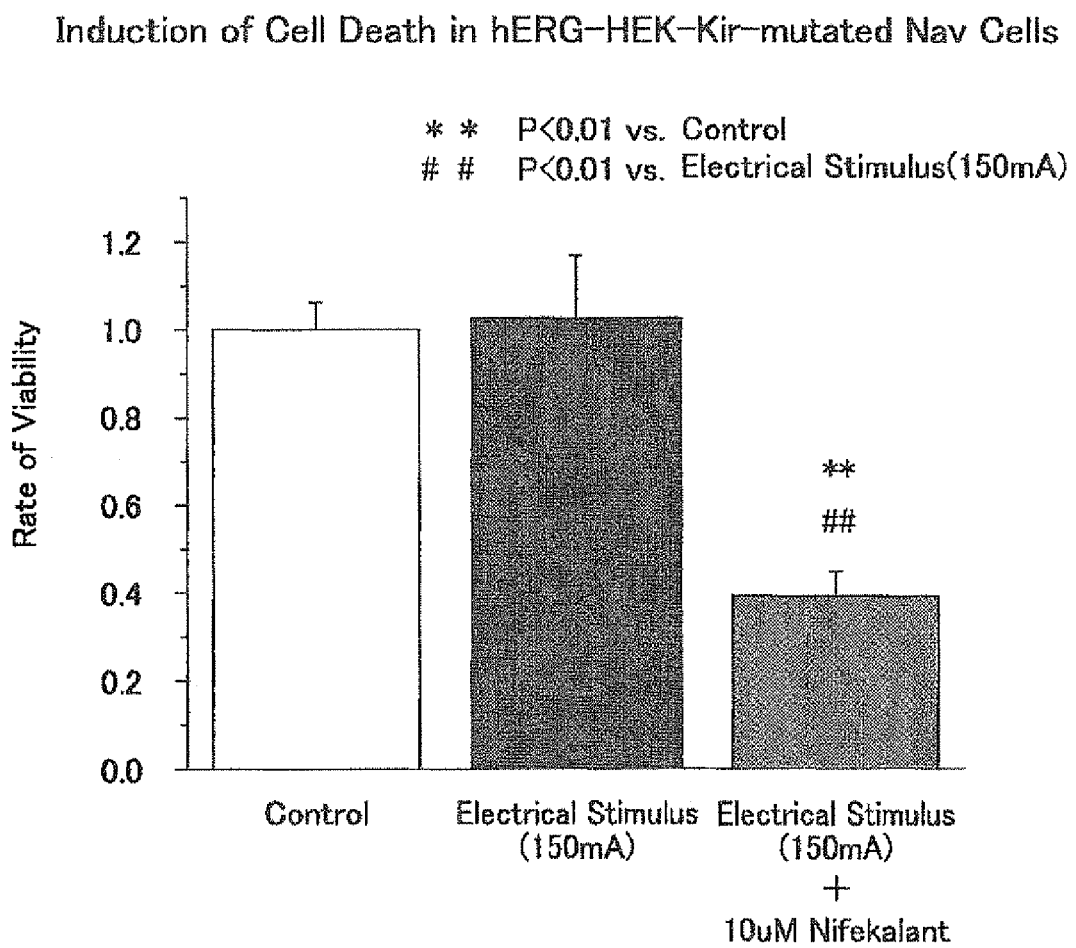
FIG. 12 is a graph indicating the induction of cell death by depolarizing stimulation resulting from administration of nifekalant in hERG-HEK-Kir-mutated Nav cells.
Figure 13:
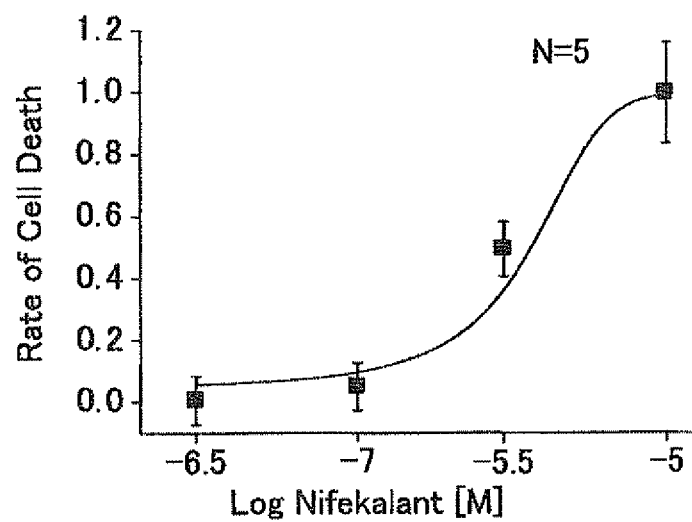
FIG. 13 is a graph indicating a dose-response curve of nifekalant based on the ratio of cell death using hERG-HEK-Kir-mutated Nav cells.

As shown in FIG. 12, although cell death was not induced even when hERG-HEK-Kir-mutated Nav cells were subjected to square wave electrical stimulation, cell death was determined to be induced by depolarizing stimulation caused by administration of nifekalant. In addition, as shown in FIG. 13, nifekalant was determined to induce cell death concentration-dependently. On the basis of the above, hERG-HEK-Kir-mutated Nav cells were determined to be preferable as a screening material for screening of compounds acting on an ion channel such as hERG monitoring cell death and the like.

Example 5

In the present example, a study was conducted on measurement of membrane potential using a membrane potential-sensitive dye in the form of $DiBAC_4(3)$, and using an extracellular solution containing K ions at a high concentration for depolarizing stimulation. $DiBAC_4(3)$ has the property of increasing in fluorescence intensity following depolarization, and demonstrates a correlation between membrane potential and changes in fluorescence intensity.

After loading two types of cells (HEK and HEK-Kir-mutated Nav cells) with 100 nM $DiBAC_4(3)$ (bis(1,3-dibutylbarbituric acid)trimethine oxanol) in normal HEPES buffer containing the dye for 30 minutes at room temperature, and fluorescence was measured at 520 nm or higher by exciting at 488 nm and reflecting with a dichroic mirror at 505 nm. In addition, high $K^+$ extracellular fluid having an increased K ion concentration was used as a stimulus to depolarize the cell membrane. This is because K ions are primarily involved in formation of resting membrane potential. Although intracellular K ion concentration is maintained at a higher level than outside cells by the Na—K pump, K ions are discharged outside the cells by leak channels. The potential at which there is a balance between the inflow of K ions by the Na—K pump and the discharge of K ions by leak channels is the resting membrane potential. Therefore, since the difference between intracellular and extracellular K ion concentrations becomes smaller when extracellular K ion concentration is increased, the resting membrane potential becomes shallow. In the present example, changes in fluorescence intensity of two types of cells were measured using this depolarizing stimulus. Furthermore, measurements were carried out based on a value of 1 for fluorescence intensity in the case of making the extracellular K ion concentration to be 140 mM $K^+$. The Argus/HiSCA high-speed, cooled CCD camera fluorescent imaging system (Hamamatsu Photonics K.K.) was used to measure fluorescence. The results are shown in FIGS. 14 to 17.

Figure 14:
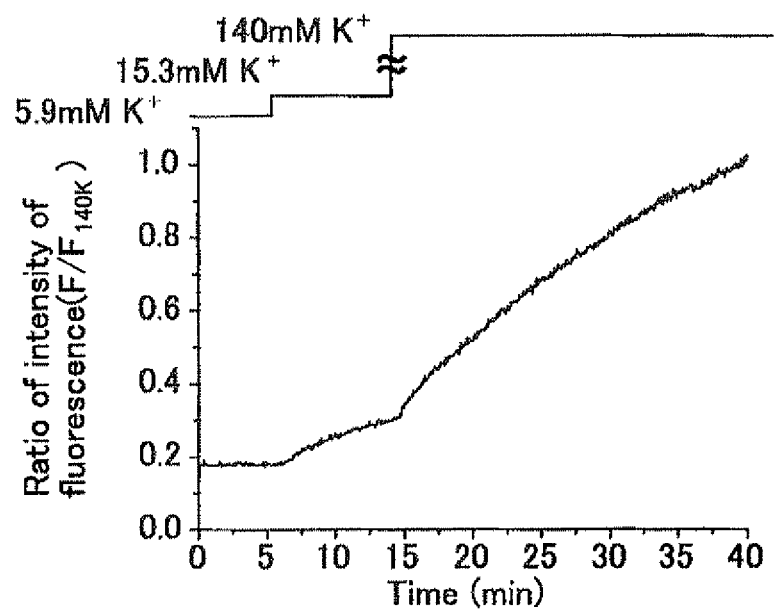
FIG. 14 is a graph indicating fluorescence changes induced by high $K^+$ stimulation in HEK-Kir cells.
Figure 15:
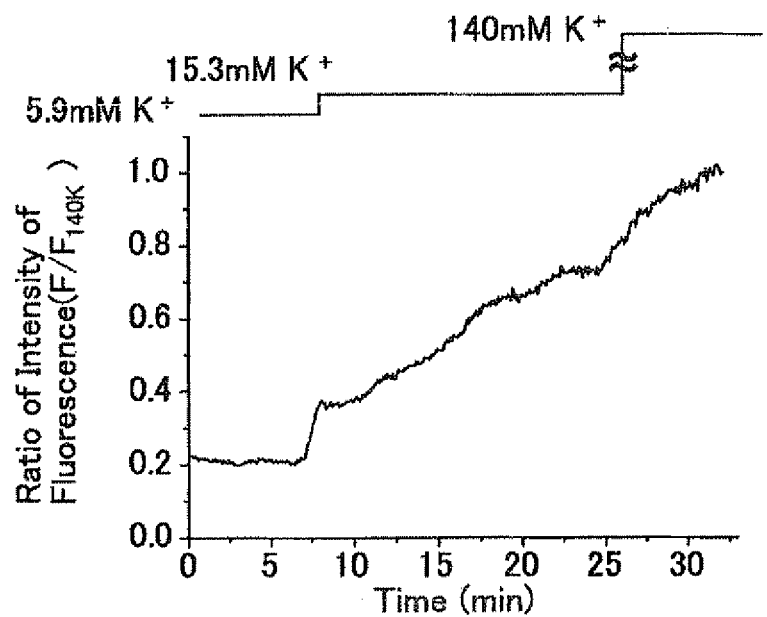
FIG. 15 is a graph indicating fluorescence changes induced by high $K^+$ stimulation in HEK-Kir-mutated Nav cells.

FIGS. 14 and 15 respectively show changes in fluorescence caused by high $K^+$ stimulation in HEK-Kir cells and HEK-Kir-mutated Nav cells (horizontal axis: time, vertical axis: fluorescence intensity and the top trace: extracellular K ion concentration). As shown in FIGS. 14 and 15, fluorescence intensity obtained from the cells was determined to increase as extracellular K ion concentration increased. Namely, extracellular K ion concentration was determined to promote depolarization of membrane potential.

Figure 16:
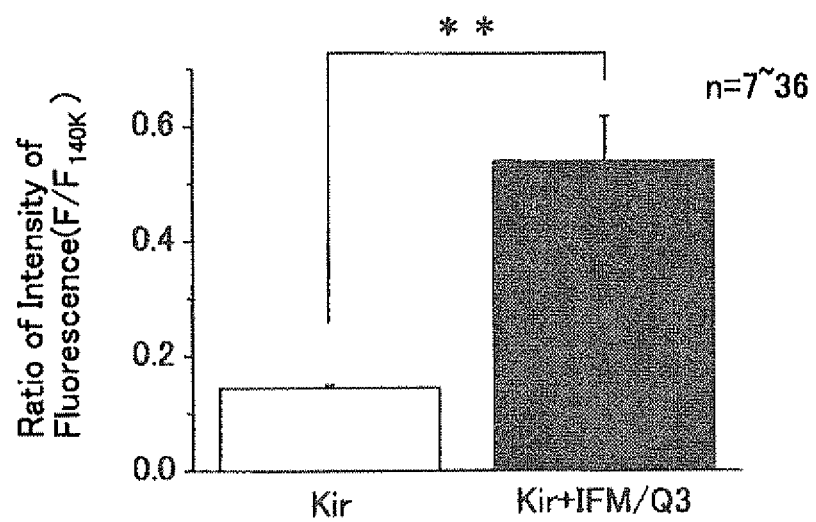
FIG. 16 is a graph indicating differences in fluorescence intensity at an extracellular $K^+$ concentration of 15.3 mM in HEK-Kir cells and HEK-Kir-mutated Nav cells.

FIG. 16 shows fluorescent intensities when the same concentrations of extracellular K ion (15.3 mM) stimulation were respectively imparted to HEK-Kir cells and HEK-Kir-mutated Nav cells. As shown in FIG. 16, HEK-Kir-mutated Nav cells demonstrated higher fluorescence intensity than HEK-Kir cells for the same K ion concentration stimulation, and were determined to be more sensitive or more susceptible to promotion of depolarization.

Figure 17:
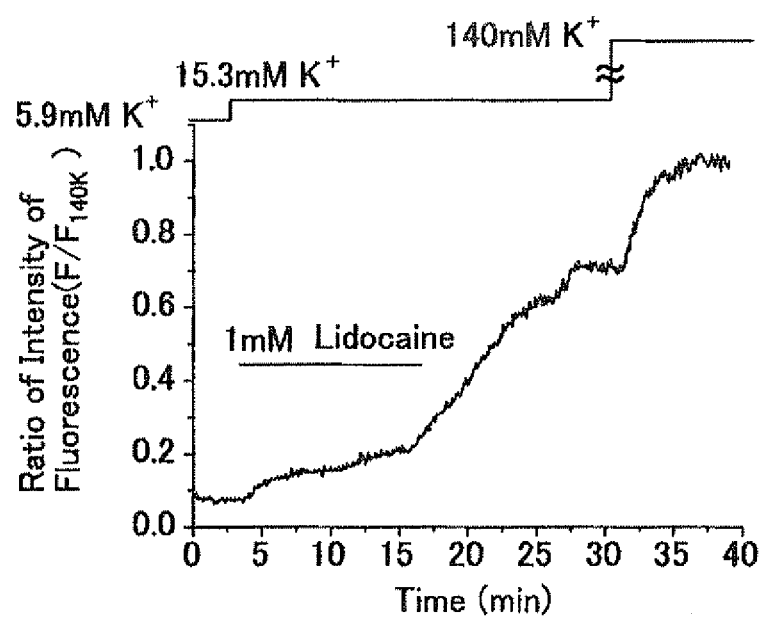
FIG. 17 is a graph indicating inhibition of high $K^+$ stimulation-induced fluorescence changes by lidocaine in HEK-Kir-mutated Nav cells.

FIG. 17 shows the effects of lidocaine administration on fluorescence intensity in HEK-Kir-mutated Nav cells in the case causing extracellular K ion concentration to change from 5.9 mM to 15.3 mM. Lidocaine is an inhibitor of Na ion channels, and in FIG. 17, the duration of administration of 1 mM lidocaine is indicated with an underline. As shown in FIG. 17, changes in fluorescence caused by stimulation with extracellular solution containing K ion concentration were determined to be inhibited by lidocaine. Furthermore, HEK-Kir-mutated Nav cells and HEK-Kir cells were confirmed to demonstrate the same changes in fluorescence in the presence of lidocaine. On the basis of the above, the inactivation-inhibited Na ion channels were determined to be involved in significant changes in fluorescence caused by K stimulation in HEK-Kir-mutated Nav cells. The present screening cells were determined to be useful in measurement of fluorescence of the membrane potential-sensitive dye, $DiBAC_4(3)$.

[Sequence Listings Free Text]
SEQ ID NO: 2 and 3: Primers
[Sequence Listings]

What is claimed is:

1. An in vitro method for screening agonists or inhibitors of a target ion channel, comprising:
   contacting a test compound with a screening material comprising
      cultured cells which express at least one first exogenous DNA encoding a Nav1.5 mutant voltage-dependent sodium (Na) ion channel that has been inhibited from being inactivated, at least one second exogenous DNA encoding a potassium (K) ion channel selected from the group consisting of Kir2.1, Kir2.2, Kir2.3, and Kir2.4 that has been activated so that a resting membrane potential becomes deeper in a negative direction, and at least one third DNA encoding a target ion channel;
      wherein the cells are configured so that the prolongation of action potential is maintained for at least 3 minutes due to the at least one first exogenous DNA and the resting membrane potential is $-70$ mV or deeper due to the at least one second exogenous DNA and thereby cell death occurs automatically due to transient induction of depolarization due to an action of the compound on the target ion channel and the action can be detected as viability and death of the cells; and
   assessing an action of the test compound on the target ion channel; and
   detecting an automatic induction of death of the cells caused by the test compound.

2. The method according to claim 1, wherein the target ion channel is an ion channel that induces depolarization of a cell membrane in the cells by activation, and the detection of an action of the test compound on the target ion channel is performed in the presence of the test compound.

3. The screening method according to claim 1, wherein the target ion channel is an ion channel that induces depolarization of the cell membrane in the cells by activation, and the detection of an action of the test compound on the target ion channel is performed in the presence of the test compound and a stimulus that acts on the target ion channel.

4. The method according to claim 1, wherein the target ion channel is an ion channel that inhibits depolarization and/or action potential of the cell membrane in the cells, and the detection of an action of the test compound on the target ion channel is performed in the presence of the test compound and a stimulus that induces depolarization of the cell membrane in the cells.

5. The method according to claim 1, wherein the target ion channel is an ion channel that inhibits depolarization of the cell membrane in the cells by activation, and the detection of an action of the test compound on the target ion channel is performed in the presence of the test compound and a stimulus that induces depolarization of the cell membrane in the cells.

6. The method of claim 1, wherein the target ion channel is a hERG ion channel.

* * * * *

SEQUENCE LISTING

```
<160> NUMBER OF SEQ ID NOS: 3

<210> SEQ ID NO 1
<211> LENGTH: 2016
<212> TYPE: PRT
<213> ORGANISM: Homo sapiens

<400> SEQUENCE: 1

Met Ala Asn Phe Leu Leu Pro Arg Gly Thr Ser Ser Phe Arg Arg Phe
1               5                   10                  15
```

```
Thr Arg Glu Ser Leu Ala Ala Ile Glu Lys Arg Met Ala Glu Lys Gln
             20                  25                  30

Ala Arg Gly Ser Thr Thr Leu Gln Glu Ser Arg Glu Gly Leu Pro Glu
         35                  40                  45

Glu Glu Ala Pro Arg Pro Gln Leu Asp Leu Gln Ala Ser Lys Lys Leu
 50                  55                  60

Pro Asp Leu Tyr Gly Asn Pro Pro Gln Glu Leu Ile Gly Pro Leu
 65                  70                  75                  80

Glu Asp Leu Asp Pro Phe Tyr Ser Thr Gln Lys Thr Phe Ile Val Leu
                 85                  90                  95

Asn Lys Gly Lys Thr Ile Phe Arg Phe Ser Ala Thr Asn Ala Leu Tyr
             100                 105                 110

Val Leu Ser Pro Phe His Pro Ile Arg Arg Ala Val Lys Ile Leu
         115                 120                 125

Val His Ser Leu Phe Asn Met Leu Ile Met Cys Thr Ile Leu Thr Asn
 130                 135                 140

Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
                 165                 170                 175

Leu Ala Arg Gly Phe Cys Leu His Ala Phe Thr Phe Leu Arg Asp Pro
             180                 185                 190

Trp Asn Trp Leu Asp Phe Ser Val Ile Ile Met Ala Tyr Thr Thr Glu
         195                 200                 205

Phe Val Asp Leu Gly Asn Val Ser Ala Leu Arg Thr Phe Arg Val Leu
 210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                 245                 250                 255

Thr Val Phe Cys Leu Ser Val Phe Ala Leu Ile Gly Leu Gln Leu Phe
             260                 265                 270

Met Gly Asn Leu Arg His Lys Cys Val Arg Asn Phe Thr Ala Leu Asn
         275                 280                 285

Gly Thr Asn Gly Ser Val Glu Ala Asp Gly Leu Val Trp Glu Ser Leu
 290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                 325                 330                 335

Glu Gly Tyr Arg Cys Leu Lys Ala Gly Glu Asn Pro Asp His Gly Tyr
             340                 345                 350

Thr Ser Phe Asp Ser Phe Ala Trp Ala Phe Leu Ala Leu Phe Arg Leu
         355                 360                 365

Met Thr Gln Asp Cys Trp Glu Arg Leu Tyr Gln Gln Thr Leu Arg Ser
 370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                 405                 410                 415

Glu Glu Gln Asn Gln Ala Thr Ile Ala Glu Thr Glu Glu Lys Glu Lys
             420                 425                 430
```

-continued

Arg Phe Gln Glu Ala Met Glu Met Leu Lys Lys Glu His Glu Ala Leu
            435                 440                 445

Thr Ile Arg Gly Val Asp Thr Val Ser Arg Ser Ser Leu Glu Met Ser
450                 455                 460

Pro Leu Ala Pro Val Asn Ser His Glu Arg Arg Ser Lys Arg Arg Lys
465                 470                 475                 480

Arg Met Ser Ser Gly Thr Glu Cys Gly Glu Asp Arg Leu Pro Lys
            485                 490                 495

Ser Asp Ser Glu Asp Gly Pro Arg Ala Met Asn His Leu Ser Leu Thr
            500                 505                 510

Arg Gly Leu Ser Arg Thr Ser Met Lys Pro Arg Ser Ser Arg Gly Ser
            515                 520                 525

Ile Phe Thr Phe Arg Arg Asp Leu Gly Ser Glu Ala Asp Phe Ala
530                 535                 540

Asp Asp Glu Asn Ser Thr Ala Gly Glu Ser Glu Ser His His Thr Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
            595                 600                 605

Pro Glu Ala Thr Ser Pro Gly Ser His Leu Leu Arg Pro Val Met Leu
610                 615                 620

Glu His Pro Pro Asp Thr Thr Thr Pro Ser Glu Glu Pro Gly Gly Pro
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
            660                 665                 670

Leu Glu Glu Leu Glu Glu Ser Arg His Lys Cys Pro Pro Cys Trp Asn
            675                 680                 685

Arg Leu Ala Gln Arg Tyr Leu Ile Trp Glu Cys Cys Pro Leu Trp Met
690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
            755                 760                 765

Ile Ala Leu Asp Pro Tyr Tyr Tyr Phe Gln Gln Gly Trp Asn Ile Phe
770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
                805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
            835                 840                 845

Ile Val Phe Ile Phe Ala Val Val Gly Met Gln Leu Phe Gly Lys Asn

```
                850                 855                 860
Tyr Ser Glu Leu Arg Asp Ser Asp Gly Leu Leu Pro Arg Trp His
865                 870                 875                 880

Met Met Asp Phe Phe His Ala Phe Leu Ile Ile Phe Arg Ile Leu Cys
                    885                 890                 895

Gly Glu Trp Ile Glu Thr Met Trp Asp Cys Met Glu Val Ser Gly Gln
                900                 905                 910

Ser Leu Cys Leu Leu Val Phe Leu Leu Val Met Val Ile Gly Asn Leu
            915                 920                 925

Val Val Leu Asn Leu Phe Leu Ala Leu Leu Leu Ser Ser Phe Ser Ala
        930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
                965                 970                 975

Thr Trp Asp Phe Cys Cys Gly Leu Leu Arg Gln Arg Pro Gln Lys Pro
                980                 985                 990

Ala Ala Leu Ala Ala Gln Gly Gln Leu Pro Ser Cys Ile Ala Thr Pro
            995                 1000                1005

Tyr Ser Pro Pro Pro Glu Thr Glu Lys Val Pro Pro Thr Arg
    1010                1015                1020

Lys Glu Thr Arg Phe Glu Gly Glu Gln Pro Gly Gln Gly Thr
    1025                1030                1035

Pro Gly Asp Pro Glu Pro Val Cys Val Pro Ile Ala Val Ala Glu
    1040                1045                1050

Ser Asp Thr Asp Gln Glu Glu Asp Glu Asn Ser Leu Gly
    1055                1060                1065

Thr Glu Glu Glu Ser Ser Lys Gln Gln Glu Ser Gln Pro Val Ser
    1070                1075                1080

Gly Gly Pro Glu Ala Pro Pro Asp Ser Arg Thr Trp Ser Gln Val
    1085                1090                1095

Ser Ala Thr Ala Ser Ser Glu Ala Glu Ala Ser Ala Ser Gln Ala
    1100                1105                1110

Asp Trp Arg Gln Gln Trp Lys Ala Glu Pro Gln Ala Pro Gly Cys
    1115                1120                1125

Gly Glu Thr Pro Glu Asp Ser Cys Ser Glu Gly Ser Thr Ala Asp
    1130                1135                1140

Met Thr Asn Thr Ala Glu Leu Leu Glu Gln Ile Pro Asp Leu Gly
    1145                1150                1155

Gln Asp Val Lys Asp Pro Glu Asp Cys Phe Thr Glu Gly Cys Val
    1160                1165                1170

Arg Arg Cys Pro Cys Cys Ala Val Asp Thr Thr Gln Ala Pro Gly
    1175                1180                1185

Lys Val Trp Trp Arg Leu Arg Lys Thr Cys Tyr His Ile Val Glu
    1190                1195                1200

His Ser Trp Phe Glu Thr Phe Ile Ile Phe Met Ile Leu Leu Ser
    1205                1210                1215

Ser Gly Ala Leu Ala Phe Glu Asp Ile Tyr Leu Glu Glu Arg Lys
    1220                1225                1230

Thr Ile Lys Val Leu Leu Glu Tyr Ala Asp Lys Met Phe Thr Tyr
    1235                1240                1245

Val Phe Val Leu Glu Met Leu Leu Lys Trp Val Ala Tyr Gly Phe
    1250                1255                1260
```

-continued

```
Lys Lys Tyr Phe Thr Asn Ala Trp Cys Trp Leu Asp Phe Leu Ile
    1265            1270            1275
Val Asp Val Ser Leu Val Ser Leu Val Ala Asn Thr Leu Gly Phe
    1280            1285            1290
Ala Glu Met Gly Pro Ile Lys Ser Leu Arg Thr Leu Arg Ala Leu
    1295            1300            1305
Arg Pro Leu Arg Ala Leu Ser Arg Phe Glu Gly Met Arg Val Val
    1310            1315            1320
Val Asn Ala Leu Val Gly Ala Ile Pro Ser Ile Met Asn Val Leu
    1325            1330            1335
Leu Val Cys Leu Ile Phe Trp Leu Ile Phe Ser Ile Met Gly Val
    1340            1345            1350
Asn Leu Phe Ala Gly Lys Phe Gly Arg Cys Ile Asn Gln Thr Glu
    1355            1360            1365
Gly Asp Leu Pro Leu Asn Tyr Thr Ile Val Asn Asn Lys Ser Gln
    1370            1375            1380
Cys Glu Ser Leu Asn Leu Thr Gly Glu Leu Tyr Trp Thr Lys Val
    1385            1390            1395
Lys Val Asn Phe Asp Asn Val Gly Ala Gly Tyr Leu Ala Leu Leu
    1400            1405            1410
Gln Val Ala Thr Phe Lys Gly Trp Met Asp Ile Met Tyr Ala Ala
    1415            1420            1425
Val Asp Ser Arg Gly Tyr Glu Glu Gln Pro Gln Trp Glu Tyr Asn
    1430            1435            1440
Leu Tyr Met Tyr Ile Tyr Phe Val Ile Phe Ile Ile Phe Gly Ser
    1445            1450            1455
Phe Phe Thr Leu Asn Leu Phe Ile Gly Val Ile Ile Asp Asn Phe
    1460            1465            1470
Asn Gln Gln Lys Lys Lys Leu Gly Gly Gln Asp Ile Phe Met Thr
    1475            1480            1485
Glu Glu Gln Lys Lys Tyr Tyr Asn Ala Met Lys Lys Leu Gly Ser
    1490            1495            1500
Lys Lys Pro Gln Lys Pro Ile Pro Arg Pro Leu Asn Lys Tyr Gln
    1505            1510            1515
Gly Phe Ile Phe Asp Ile Val Thr Lys Gln Ala Phe Asp Val Thr
    1520            1525            1530
Ile Met Phe Leu Ile Cys Leu Asn Met Val Thr Met Met Val Glu
    1535            1540            1545
Thr Asp Asp Gln Ser Pro Glu Lys Ile Asn Ile Leu Ala Lys Ile
    1550            1555            1560
Asn Leu Leu Phe Val Ala Ile Phe Thr Gly Glu Cys Ile Val Lys
    1565            1570            1575
Leu Ala Ala Leu Arg His Tyr Tyr Phe Thr Asn Ser Trp Asn Ile
    1580            1585            1590
Phe Asp Phe Val Val Val Ile Leu Ser Ile Val Gly Thr Val Leu
    1595            1600            1605
Ser Asp Ile Ile Gln Lys Tyr Phe Phe Ser Pro Thr Leu Phe Arg
    1610            1615            1620
Val Ile Arg Leu Ala Arg Ile Gly Arg Ile Leu Arg Leu Ile Arg
    1625            1630            1635
Gly Ala Lys Gly Ile Arg Thr Leu Leu Phe Ala Leu Met Met Ser
    1640            1645            1650
```

Leu Pro Ala Leu Phe Asn Ile Gly Leu Leu Leu Phe Leu Val Met
1655                     1660                1665

Phe Ile Tyr Ser Ile Phe Gly Met Ala Asn Phe Ala Tyr Val Lys
1670                    1675                1680

Trp Glu Ala Gly Ile Asp Asp Met Phe Asn Phe Gln Thr Phe Ala
1685                    1690                1695

Asn Ser Met Leu Cys Leu Phe Gln Ile Thr Thr Ser Ala Gly Trp
1700                    1705                1710

Asp Gly Leu Leu Ser Pro Ile Leu Asn Thr Gly Pro Pro Tyr Cys
1715                    1720                1725

Asp Pro Thr Leu Pro Asn Ser Asn Gly Ser Arg Gly Asp Cys Gly
1730                    1735                1740

Ser Pro Ala Val Gly Ile Leu Phe Phe Thr Thr Tyr Ile Ile Ile
1745                    1750                1755

Ser Phe Leu Ile Val Val Asn Met Tyr Ile Ala Ile Ile Leu Glu
1760                    1765                1770

Asn Phe Ser Val Ala Thr Glu Glu Ser Thr Glu Pro Leu Ser Glu
1775                    1780                1785

Asp Asp Phe Asp Met Phe Tyr Glu Ile Trp Glu Lys Phe Asp Pro
1790                    1795                1800

Glu Ala Thr Gln Phe Ile Glu Tyr Ser Val Leu Ser Asp Phe Ala
1805                    1810                1815

Asp Ala Leu Ser Glu Pro Leu Arg Ile Ala Lys Pro Asn Gln Ile
1820                    1825                1830

Ser Leu Ile Asn Met Asp Leu Pro Met Val Ser Gly Asp Arg Ile
1835                    1840                1845

His Cys Met Asp Ile Leu Phe Ala Phe Thr Lys Arg Val Leu Gly
1850                    1855                1860

Glu Ser Gly Glu Met Asp Ala Leu Lys Ile Gln Met Glu Glu Lys
1865                    1870                1875

Phe Met Ala Ala Asn Pro Ser Lys Ile Ser Tyr Glu Pro Ile Thr
1880                    1885                1890

Thr Thr Leu Arg Arg Lys His Glu Glu Val Ser Ala Met Val Ile
1895                    1900                1905

Gln Arg Ala Phe Arg Arg His Leu Leu Gln Arg Ser Leu Lys His
1910                    1915                1920

Ala Ser Phe Leu Phe Arg Gln Gln Ala Gly Ser Gly Leu Ser Glu
1925                    1930                1935

Glu Asp Ala Pro Glu Arg Glu Gly Leu Ile Ala Tyr Val Met Ser
1940                    1945                1950

Glu Asn Phe Ser Arg Pro Leu Gly Pro Pro Ser Ser Ser Ser Ile
1955                    1960                1965

Ser Ser Thr Ser Phe Pro Pro Ser Tyr Asp Ser Val Thr Arg Ala
1970                    1975                1980

Thr Ser Asp Asn Leu Gln Val Arg Gly Ser Asp Tyr Ser His Ser
1985                    1990                1995

Glu Asp Leu Ala Asp Phe Pro Pro Ser Pro Asp Arg Asp Arg Glu
2000                    2005                2010

Ser Ile Val
2015

<210> SEQ ID NO 2
<211> LENGTH: 40
<212> TYPE: DNA

```
<213> ORGANISM: Artificial
<220> FEATURE:
<223> OTHER INFORMATION: Synthetic Construct - primer

<400> SEQUENCE: 2
gttagggggc caggaccaac aacagacaga ggagcagaag                              40

<210> SEQ ID NO 3
<211> LENGTH: 40
<212> TYPE: DNA
<213> ORGANISM: Artificial
<220> FEATURE:
<223> OTHER INFORMATION: Synthetic Construct - primer

<400> SEQUENCE: 3
cttctgctcc tctgtctgtt gttggtcctg gccccctaac                              40
```